US008829272B2

(12) United States Patent
Lopato et al.

(10) Patent No.: US 8,829,272 B2
(45) Date of Patent: Sep. 9, 2014

(54) SPECIFIC EXPRESSION USING TRANSCRIPTIONAL CONTROL SEQUENCES IN PLANTS

(75) Inventors: Sergiy Lopato, Morphett Vale (AU); Ming Li, Myrtle Bank (AU)

(73) Assignees: Adelaide Research & Innovation Pty Ltd (AU); Grains Research & Development Corporation (AU)

( * ) Notice: Subject to any disclaimer, the term of this patent is extended or adjusted under 35 U.S.C. 154(b) by 1100 days.

(21) Appl. No.: 12/091,401

(22) PCT Filed: Oct. 27, 2006

(86) PCT No.: PCT/AU2006/001618
§ 371 (c)(1),
(2), (4) Date: Sep. 8, 2008

(87) PCT Pub. No.: WO2007/048207
PCT Pub. Date: May 3, 2007

(65) Prior Publication Data
US 2009/0158457 A1    Jun. 18, 2009

(30) Foreign Application Priority Data
Oct. 27, 2005    (AU) ................................ 2005905933

(51) Int. Cl.
*C12N 15/82*    (2006.01)
*C07H 21/04*    (2006.01)

(52) U.S. Cl.
USPC ........... 800/278; 800/298; 800/320; 536/24.1

(58) Field of Classification Search
USPC ............................................... 800/278–323.3
See application file for complete search history.

(56) References Cited

U.S. PATENT DOCUMENTS

2004/0016025 A1 *   1/2004   Budworth et al. ............ 800/287

OTHER PUBLICATIONS

Li et al_Plant Biotech J_6_465_2008.*
Donald_EMBO J_9_1717_1990.*
Dolferus_Plant Phys_105_1075_1994.*
Kim_Plant Mol Biol_24_105_1994.*
Sasaki, et al., "The genome sequence and structure of rice chromosome 1," (bases 33267-36075; 97.6% identity), NCBI, GenBank Acc. No. AP003221, 53 pgs. (last updated Nov. 3, 2004).
Sasaki, et al., "The genome sequence and structure of rice chromosome 1," (bases 140871-143679; 97.6% identity), NCBI, GenBank Acc. No. AP003293, 55 pgs. (last updated Nov. 3, 2004).

* cited by examiner

*Primary Examiner* — Medina A Ibrahim
*Assistant Examiner* — Russell Boggs
(74) *Attorney, Agent, or Firm* — Kilpatrick Townsend & Stockton LLP

(57) ABSTRACT

The present invention relates generally to methods and transcriptional control sequences suitable for effecting expression of a nucleotide sequence of interest in a plant. More particularly, the present invention relates to methods and transcriptional control sequences suitable for directing specific or preferential expression of a nucleotide sequence of interest in a plant seed. Of particular interest as a transcriptional control sequence in this invention is the promoter PR602 (SEQ ID NO: 1) found in the 5'-untranslated region of the rice END1-like gene and isolated from a rice panicle library.

6 Claims, 9 Drawing Sheets

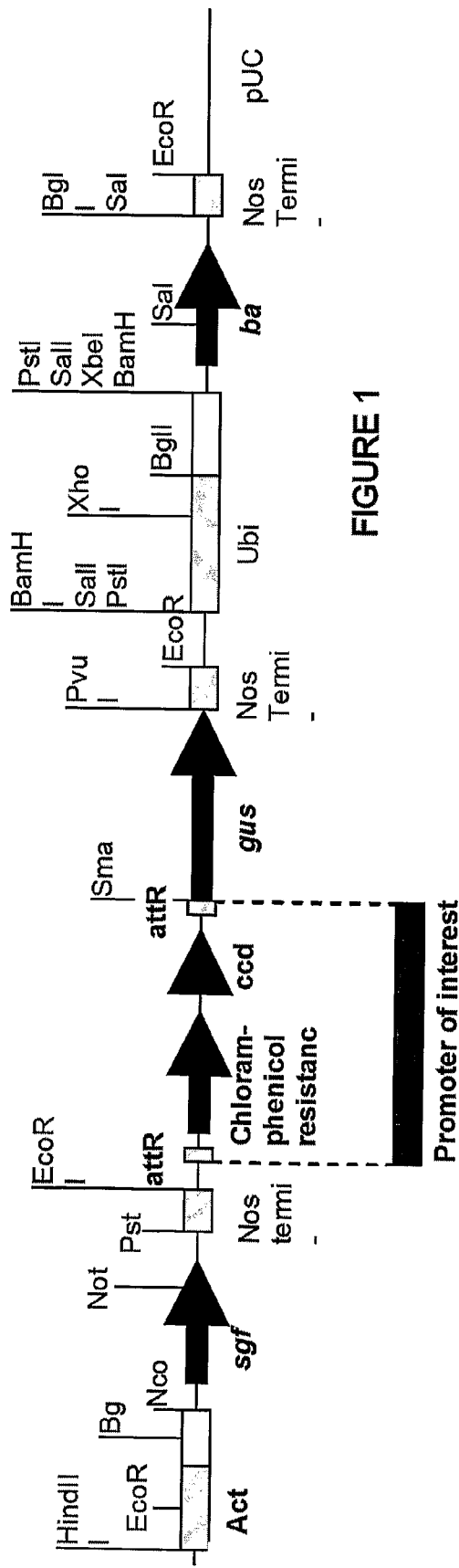

FIGURE 3

```
-3079                 GCACTCAAAA CGAGAAAACT CATTGACACG
-2779      TGATTAATTA AGTATTAATC TCTATATCTT CTCTACTATT ATAAAAACTG
-2729      AAGAAGTATT TGTCAGTAAT TTGGTACATC ATCCGTGTAT GAGTTGGTTT
-2679      TTAAATTCGT TCGCTTTTTG AAATACAGAA GGTGTCGTAT AAGAAATATA
-2629      TTTAAAAAAC TCGCATGCTA ACTTGAGACG ATCGGACTTC TAACTGCAGC
-2579      TTATGATTTT CTAAAAAAAA ATATGTTCTT TTTTTGCGAG GAAAAAGATA
-2529      TATGTTCAAG TGAATTCTCA GGGAGAATTT CACTTTAGCT AAACCATATA
-2479      ACAATAATAA TATTAAAATA GTCTTTACCC GTTACAACGC ACGGGCATTT
-2429      TTCTAGTCAT TTGAAAATTT TAAAAATATG TTTATTCAAA TAGATCTAAG
-2379      AACTTCTAAA ACATATTTGG ACATGCAAAC AATCTCAAGT GAAAGGTCAT
-2329      TAACTTCAAA GTTGTAGATT TCGTCGAGCT CTACAATTTT GATATAAAGT
-2279      TGGTTTTCAT CCAACAACCT CATATGAGAA AGTGGTTTCT AAAAAAATAT
-2229      GCACATATGA TATGAGTAGG TCCATTTCTA AAGGCACACC TCTCAAAATA
-2179      AAATTTTAGA GGTGATCGCT TAAGGCAACC GCCTCTAGAA TTGAGGAGGC
-2129      AATTAAGACG ATCGCCTCTA AAAATCTATT TTATAGGTGA TTTTCTAATG
-2079      CAGTTACATA GACCATTCAT CACTAGAAAT CAGGCTATTT TTAAAGTTGA
-2029      TCTGTTTATA TGGCTGCCTC TAAAAATCAA TGTCTAGTGG TTGTCCATGA
-1979      CTGCGGGTCC ATTATATACG TTGGTTTTCT TATAAACTAT ATGTACAGTA
-1929      ACAATCACGA TAATTTAATA TATGTGGTCT CTTAGTTTAT GTGTGTGTAC
-1879      GGTGTGTGTA TTTATTTGTT TCTTTGCATC TCCATAATCA TGGTTATTTT
-1829      GAATGGTTTG TTTTTCAGGC TACCGTGTTC CTGCTTCCCT CGCTTAATGC
-1779      TTATGTGTCC TGCCAGTTGC ATTATCACGG ATAACTGATC ATATGCCATT
-1729      TTATGGCTTC AGTCATAATA TATTGTTTTA CTAAGTTTGT CTACATGATA
-1679      AAGAGATACA CATGGATCTC TCCTAAATAA AGTCATCATT GATGTCCACA
-1629      TGCATTATTA TGTATGTTAA TTTACAAGTG ATAAAACACA TACTACTACT
-1579      ACACCCAAGA TGTGGTATAG CTCAAACACA CCCCAACGTA GTAATTTTTC
-1529      TAGTGAGAGA ACAATCATAT ATAGCAAAAT ATCCTATTGA GCCTGGCGAT
-1479      AATAACTCAT AGTAATAATT TTATTATGTA AGAAGTTTGT TTTTAGTTAT
-1429      CACACACACT GGGTGCATCT TAATGCTATA TATTTATTTG GCCACACAAA
-1379      AGTAGTTCTT CCTCTAATGC CTTTCATTCT CAACTTTCAT CATTTATTTG
-1329      TCCTTTTTGT TAGGTTCCGT CAACCTAATA TGGGTGAAAA GACAGTTTTC
-1279      TATTAATATG TTTTAATGCA AGATCTGTGA TTTTTATATT TTCTTTTGAG
-1229      TTACAATTTT TATACTAGCT TATTATGCAT GATGGTCGAA TATCTCTCAT
-1179      GAACCATAAT ATTATTTTAG TAATCAAGTG TGATGCAAAA TCCTTTAAAT
-1129      TTAGTATATT ACATAAAAAA ATAATTCTCA ATTTCTACTT CTTAGCTTAT
-1079      AGGCTGTGCG CATATAGAAT TTGAATTTTA GAAGTTTAA AGTTGATTTT
-1029      GGTTTTTTAT CATATTTATT TTTAGCACTG ACTTTTGAAT AGCTAAAATT
-979       GAAAAACTTA TCGTAAAAAA TATTATTATT GGTTGCTTCG TTTATTCTGG
-929       ATGCATCTTA ACATTACTG TAAAAATATA ACCTATGGTT TACTTATATT
-879       TAATCAACAA TATTTATTGT TAAAAAGTAA TAGACAAGAG AAAAACAATC
-829       TTTTCTTCCA TCTATTAACA TTATGTTAAT GGACAACTAA CGGAAAGGGC
-779       AAATAAGATA TCAAATTTAA GAATAAGTGT ATAAGAGGGG AAGCCAATTT
-729       TGTGAGAATA AATAAGGAAC CGATCAAGTC TAGAGGACAC ATAAAGAATT
-679       TTCTCATCAT GGTGTTCATA TAACTAGCCC GTTGAACTGT GAGATTGAAT
-629       ACTTTTGGGA TAGTGAAAGA ATATTTGACT TAATATTTTT CTTGAACACT
-579       ACAATCTGCT ATTTGTTTCA CATATAAAAA AGTGAATATT GCATCCTCAA
-529       TAAATGATCT AACATAAGGT ACATAAATAT CTAAATCTTT CTCTATTAAT
-479       GTGTCATACA TGGATGCATA TATCTTAGTA AATATCTAAA TCTTTCTCTA
-429       TTAATGTGTG GATTCATACA TGGATGCATA TATCTTCAAT AAGTGAGTAG
-379       TAAATATCTA AATCTTTCTC TATTAATGTG TGGATTCATA CATGGATGCA
-329       TATATCTTCA ATAAATGAGT AGCAAATGTT TAAATCTTTT CTTTATTAAT
```

FIGURE 3 (cont)

```
-279    GTGTGGGTTC  AACATGCATG  GATGCATATA  TCTTTAATAA  ATGAGCCAAT
-229    TAAATATGAG  GTGCACAAAT  ATCCAAATCT  TTGCATGCAT  AGGCTCTCTC
-179    TTCACCATTG  ATTTTACATC  CAATGGATAC  AATTCGAGCA  ACATGTCAAC
-129    TTTTCCCCTC  GATGGCCTTA  TATAAACCCA  ACTATCCCCA  ACTAGAAGAT
-79     ACACACCACA  ACAATATAGC  CACTGTATTG  ATATCAAGAA  AAAGGTCTAT
                                             M   G   K   L   Y   G   L
-29     CCTAGCTGCT  TTATAGTAAA  GCAATAGCCA  TGGGAAAGCT  TTATGGTTTG
         F   W   V   M   A   L   V   L   A   T   V   A   G   T   K   S   D ·
 22     TTCTGGGTTA  TGGCCTTGGT  ATTGGCTACG  GTGGCTGGTA  CAAAATCCGA
       · E   G   C   S   R   D   L   Q   D   L   I   M   E   C   Q   K   Y ·
 72     TGAGGGTTGC  AGTCGTGATC  TTCAGGACTT  AATTATGGAG  TGTCAAAAAT
       · V   M   N   P   A   N   P   K   I   E   P   S   N   A   C   C
122     ATGTTATGAA  TCCTGCAAAC  CCAAAGATAG  AACCCTCAAA  CGCATGCTGT
         S   V   I   Q   K   A   N   V   P   C   L   C   S   K   V   T   K ·
172     AGCGTAATCC  AAAAGGCAAA  CGTCCCATGT  TTATGCTCCA  AGGTCACTAA
       · E   I   E   K   I   V   C   M   E   K   V   V   Y   V   A   D   Y ·
222     AGAGATTGAG  AAGATAGTGT  GCATGGAGAA  GGTCGTGTAT  GTTGCTGACT
       · C   K   K   P   L   Q   P   G   S   K   C   G
272     ATTGCAAGAA  GCCACTACAG  CCTGGCTCCA  AGTGTGGAAG  TAAGCTTTAA
322     TACAAACTCA  ACAAAAGCAT  TTGTGTTGT   TTATGAATT   GTCAATGATA
                                                       Y   T   I   P   S   L ·
372     TTTATTATTT  TCTTCTGAAT  TACGTTTGCA  GGCTACACGA  TTCCGTCTCT
       · Q   Q   *
422     ACAACAATAA  TTGGATATGA  TCAAGCATGA  AGATGATGGC  TTTGTCTTTT
472     AGGATAAGTC  TAATTTGTGA  GGTTGTCCAT  TGGCAATAAT  CTATTTTGAG
522     TCATTTGTGG  GCAATTGTGG  CCAATGTGAG  TCGGATATTT  AATATTGTAA
572     AATAAATATT  AAAAATGAAC  AAATAATGTC  TTTTAGATTT  TCTATCTTTT
622     CAGATGACTA  GATGGCGCCT  CTAACCTTCA  TCTTCCACGT  GGCGGTTCCC
672     CATAGGCTCT  CAATGACGGT  TGCAAGTGAA  TCGACGTTGG  AAACCGCCAT
```

SPECIFIC EXPRESSION USING TRANSCRIPTIONAL CONTROL SEQUENCES IN PLANTS

CROSS-REFERENCES TO RELATED APPLICATIONS

This application is a U.S. National Stage Application of PCT/AU2006/001618, filed Oct. 27, 2006, which claims the benefit of Australian Application No. 2005905933, filed Oct. 27, 2005.

FIELD OF THE INVENTION

The present invention relates generally to methods and transcriptional control sequences suitable for effecting expression of a nucleotide sequence of interest in a plant. More particularly, the present invention relates to methods and transcriptional control sequences suitable for directing specific or preferential expression of a nucleotide sequence of interest in a plant seed.

BACKGROUND OF THE INVENTION

The primary emphasis in genetic modification has been directed to prokaryotes and mammalian cells. For a variety of reasons, plants have proven more intransigent than other eukaryotic cells to genetically manipulate. However, in many instances, it is desirable to effect transcription of an introduced nucleotide sequence of interest either specifically or preferentially in a particular plant part or at a particular developmental stage of the plant. Accordingly, there is a substantial interest in identifying transcriptional control sequences, such as promoters or enhancers, which specifically or preferentially direct transcription in particular plant organs, tissues or cell types or at particular developmental stages of the plant.

Expression of heterologous DNA sequences in a plant is dependent upon the presence of an operably linked transcriptional control sequence, such as a promoter or enhancer, which is functional within the plant. The choice of transcriptional control sequence will determine when and where within the organism the heterologous DNA sequence is expressed. For example, where continuous expression is desired throughout the cells of a plant, constitutive promoters are utilised. In contrast, where gene expression in response to a stimulus is desired, an inducible promoter may be used. Where expression in specific tissues or organs is desired, a tissue-specific promoter may be used.

Frequently, it is desirable to effect expression of a DNA sequence in particular tissues or organs of a plant. For example, increased nutritional value of a plant might be accomplished by genetic manipulation of the plant's genome with a seed-preferred promoter operably linked to a heterologous gene such that proteins with enhanced amino acid content are produced in the seed of the plant.

Alternatively, it might be desirable to inhibit expression of a native DNA sequence within particular plant tissues to achieve a desired phenotype. In this case, such inhibition might be accomplished by transformation of the plant with a tissue-specific promoter operably linked to an antisense nucleotide sequence, such that expression of the antisense sequence produces an RNA transcript that interferes with translation of the mRNA of the native DNA sequence.

Thus, isolation and characterisation of seed-specific or seed-preferential transcriptional control sequences, which can serve as regulatory regions for expression of heterologous nucleotide sequences of interest in a seed, would be desirable for use in the genetic manipulation of plants.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification of a transcriptional control sequence which is active in plants, the transcriptional control sequence comprising the nucleotide sequence as set forth in SEQ ID NO: 1, or a functionally active fragment or variant thereof.

Generally, the transcriptional control sequences of the present invention direct seed-specific or seed-preferential expression of an operably connected nucleotide sequence of interest.

Accordingly, in a first aspect, the present invention provides a method for specifically or preferentially expressing a nucleotide sequence of interest in a plant seed, the method comprising effecting transcription of the nucleotide sequence of interest in a plant under the transcriptional control of a transcriptional control sequence comprising the nucleotide sequence set forth in SEQ ID NO: 1 or a functionally active fragment or variant thereof; wherein the nucleotide sequence of interest is heterologous with respect to SEQ ID NO: 1.

In some embodiments the transcriptional control sequence directs specific or preferential expression of a nucleotide sequence of interest in one or more of the endosperm tissue, the nucellar projection, the Endosperm Transfer Layer (ETL) or the crease aleurone in a seed.

The present invention contemplates the specific or preferential expression of a nucleotide sequence of interest in any plant seed. In some specific embodiments of the invention, the plant is a monocotyledonous plant, a cereal crop plant or a barley, wheat or rice plant.

In a second aspect, the present invention provides a nucleic acid construct comprising a transcriptional control sequence comprising the nucleotide sequence set forth in SEQ ID NO: 1 or a functionally active fragment or variant thereof.

The nucleic acid construct may further comprise a nucleotide sequence of interest, which is heterologous with respect to SEQ ID NO: 1, wherein the nucleotide sequence of interest is operably connected to the transcriptional control sequence. In a further embodiment, the nucleic acid construct may further comprise a nucleotide sequence defining a transcription terminator.

In one specific embodiment, the nucleic acid construct of the present invention comprises an expression cassette having the structure:

wherein:

$[N]_w$ comprises one or more nucleotide residues, or is absent;
TCS defines a transcriptional control sequence comprising the nucleotide sequence set forth in SEQ ID NO: 1, or a functionally active fragment or variant thereof;
$[N]_x$ comprises one or more nucleotide residues, or is absent;
SoI comprises a nucleotide sequence of interest that is heterologous with respect to SEQ ID NO: 1, which encodes an mRNA or non-translated RNA, wherein the nucleotide sequence, SoI, is operably connected to the transcriptional control sequence, TCS;
$[N]_y$ comprises one or more nucleotide residues, or is absent;
TT comprises a nucleotide sequence defining a transcription terminator;
$[N]_z$ comprises one or more nucleotide residues, or is absent.

In a third aspect, the present invention provides a cell comprising the nucleic acid construct of the second aspect of the invention or a genomically integrated form thereof.

The cell may be any plant cell, and in some specific embodiments of the invention may be a monocot plant cell, a cereal crop plant cell or a barley, wheat or rice cell. In another embodiment, the cell of the present invention may also comprise a prokaryotic cell.

In a fourth aspect, the present invention contemplates a multicellular structure comprising one or more cells of the third aspect of the invention.

In one embodiment, the multicellular structure comprises a plant or a part, organ or tissue thereof. In some specific embodiments of the invention, the plant or a part, organ or tissue thereof comprises a monocot plant or a part, organ or tissue thereof, a cereal crop plant or a part, organ or tissue thereof or a barley, wheat or rice plant or a part, organ or tissue thereof.

In one specific embodiment, the multicellular structure comprises a plant seed, and in some embodiments the nucleotide sequence of interest is specifically or preferentially expressed in the seed. In further embodiments the nucleotide sequence of interest is specifically or preferentially expressed in one or more of the endosperm tissue, the nucellar projection, the Endosperm Transfer Layer (ETL) or the crease aleurone in a seed.

In a fifth aspect, the present invention provides an isolated nucleic acid molecule comprising the nucleotide sequence set forth in SEQ ID NO: 1, or a functionally active fragment or variant thereof, wherein the nucleotide sequence defines a transcriptional control sequence.

In one embodiment the transcriptional control sequence specifically or preferentially directs the expression of an operably connected nucleotide sequence in a plant seed. In further embodiments the transcriptional control sequence directs specific or preferential expression of a nucleotide sequence of interest in one or more of the endosperm tissue, the nucellar projection, the Endosperm Transfer Layer (ETL) or the crease aleurone in a seed.

In further embodiments, the transcriptional control sequence specifically or preferentially directs the expression of an operably connected nucleotide sequence in a monocot plant seed, a cereal crop plant seed or a barley, rice or wheat seed.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). The SEQ ID NOs: correspond numerically to the sequence identifiers <400> 1 (SEQ ID NO: 1), <400> 2 (SEQ ID NO: 2), etc. A summary of the sequence identifiers is provided in Table 1. A sequence listing is also provided at the end of the specification.

TABLE 1

| Summary of Sequence Identifiers | |
|---|---|
| Sequence Identifier | Sequence |
| SEQ ID NO: 1 | PR602 promoter nucleotide sequence |
| SEQ ID NO: 2 | C_PR602 primer nucleotide sequence |
| SEQ ID NO: 3 | PR602r primer nucleotide sequence |
| SEQ ID NO: 4 | GUS5'rev primer nucleotide sequence |

DESCRIPTION OF EXEMPLARY EMBODIMENTS

It is to be understood that the following description is for the purpose of describing particular embodiments only and is not intended to be limiting with respect to the above description.

As set out above, the present invention is predicated, in part, on the identification of transcriptional control sequences which are active in plants.

As used herein, the term "transcriptional control sequence" should be understood as a nucleotide sequence that modulates at least the transcription of an operably connected nucleotide sequence. Furthermore, the transcriptional control sequence of the present invention may comprise any one or more of, for example, a leader, promoter, enhancer or upstream activating sequence. As referred to herein, the term "transcriptional control sequence" generally at least includes a promoter. A "promoter" as referred to herein, encompasses any nucleic acid that confers, activates or enhances expression of an operably connected nucleotide sequence in a cell.

As used herein, the term "operably connected" refers to the connection of a transcriptional control sequence, such as a promoter, and a nucleotide sequence of interest in such as way as to bring the nucleotide sequence of interest under the transcriptional control of the transcriptional control sequence. For example, promoters are generally positioned 5' (upstream) of a nucleotide sequence to be operably connected to the promoter. In the construction of heterologous transcriptional control sequence/nucleotide sequence of interest combinations, the promoter is generally positioned at a distance from the transcription start site that is approximately the same as the distance between that promoter and the gene it controls in its natural setting, ie. the gene from which the promoter is derived. As is known in the art, some variation in this distance can be accommodated without loss of promoter function.

Accordingly, in a first aspect, the present invention provides a method for specifically or preferentially expressing a nucleotide sequence of interest in a plant seed, the method comprising effecting transcription of the nucleotide sequence of interest in a plant under the transcriptional control of a transcriptional control sequence comprising the nucleotide sequence set forth in SEQ ID NO: 1 or a functionally active fragment or variant thereof; wherein the nucleotide sequence of interest is heterologous with respect to SEQ ID NO: 1.

As set out above, the method of the present invention contemplates specific or preferential expression of the nucleotide sequence of interest in the seed of a plant. As used herein, "specifically expressing" means that the nucleotide sequence of interest is expressed substantially only in the seed of a plant. "Preferentially expressing" should be understood to mean that nucleotide sequence of interest is expressed at a higher level in a seed of the plant than in one or more other tissues of the plant, eg. leaf tissue or root tissue. In some embodiments, preferential expression in a seed includes expression of a nucleotide sequence of interest in the seed at a level of at least twice, at least 5 times or at least 10 times the level of expression seen in at least one other tissue of the plant.

As referred to herein, "expression" of a nucleotide sequence in a plant seed refers to the transcription and/or translation of a nucleotide sequence in one or more cells of the plant seed. This definition in no way implies that expression of the nucleotide sequence must occur in all cells of the plant seed. As set out below, in some embodiments, the present invention also contemplates expression of a nucleotide sequence in particular parts of a plant seed (such as the endosperm tissue, the nucellar projection, the Endosperm Transfer Layer (ETL) or the crease aleurone). In these embodiments, it should also be understood that expression of a nucleotide sequence in these parts of the seed refers to expression in one or more cells of these parts of the seed, and not necessarily in all cells that make up the mentioned part of the seed.

As set out above, the transcriptional control sequences of the present invention comprise the nucleotide sequence set forth in SEQ ID NO: 1 or a functionally active fragment or variant thereof. As referred to herein, a "functionally active fragment or variant" refers to a fragment or variant of the nucleotide sequence set forth in SEQ ID NO: 1 which substantially retains the ability to specifically or preferentially direct expression of an operably connected nucleotide sequence in a plant seed.

"Functionally active fragments" of the transcriptional control sequence of the invention may be of any length wherein the transcriptional control sequence retains the capability to direct seed specific or seed preferential expression of an operably connected nucleotide sequence. In various embodiments, the fragment is at least 100 nucleotides (nt), at least 200 nt, at least 500 nt, at least 1000 nt, at least 1500 nt or at least 2000 nt in length. A fragment "at least 100 nt in length" includes, for example, fragments which include 100 or more contiguous bases from the nucleotide sequence of SEQ ID NO: 1.

"Functionally active variants" of the transcriptional control sequence of the invention include orthologs, mutants, synthetic variants, analogs and the like which retain the capability to direct seed specific or seed preferential expression of an operably connected nucleotide sequence. For example, the term "variant" should be considered to specifically include transcriptional control sequences which are orthologous to SEQ ID NO: 1 from other organisms; mutants of the transcriptional control sequence of SEQ ID NO: 1; variants of SEQ ID NO: 1 wherein one or more of the nucleotides within the sequence has been substituted, added or deleted; and analogs that contain one or more modified bases or DNA or RNA backbones modified for stability or for other reasons. "Modified" bases include, for example, tritylated bases and unusual bases such as inosine.

In one embodiment the functionally active fragment or variant directs specific or preferential expression of an operably connected nucleotide sequence in one or more of the endosperm tissue, the nucellar projection, the Endosperm Transfer Layer (ETL) or the crease aleurone in a seed.

In further embodiments, the functionally active fragment or variant comprises at least 50%, at least 65%, at least 80% or at least 95% sequence identity to the nucleotide sequence set forth in SEQ ID NO: 1.

When comparing nucleic acid sequences to calculate a percentage identity, the compared nucleotide sequences should be compared over a comparison window of at least 100 nucleotide residues, at least 200 nucleotide residues, at least 500 nucleotide residues, at least 1000 nucleotide residues or over the full length of SEQ ID NO: 1. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

In another embodiment, the functionally active fragment or variant comprises a nucleic acid molecule which hybridises to a nucleic acid molecule comprising the nucleotide sequence set forth in SEQ ID NO: 1 under stringent conditions.

As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilising agents such as formamide. Stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridisation is generally less than about 24 hours, usually about 4 to about 12 hours.

Specificity of hybridisation is typically the function of post-hybridisation washes, the critical factors being the ionic strength and temperature of the final wash solution. For DNA-DNA hybrids, the $T_m$ can be approximated from the equation of Meinkoth and Wahl (*Anal. Biochem.* 138: 267-284, 1984), ie. $T_m = 81.5°$ C. $+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridisation solution, and L is the length of the hybrid in base pairs. The $T_m$ is the temperature (under defined ionic strength and pH) at which 50% of a complementary target sequence hybridises to a perfectly matched probe. $T_m$ is reduced by about 1° C. for each 1% of mismatching; thus, $T_m$, hybridisation, and/or wash conditions can be adjusted to hybridise to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilise a hybridisation and/or wash at, for example, 1, 2, 3, or 4° C. lower than the thermal melting point ($T_m$); medium stringency conditions can utilise a hybridisation and/or wash at, for example, 6, 7, 8, 9, or 10° C. lower than the thermal melting point ($T_m$); low stringency conditions can utilise a hybridisation and/or wash at, for example, 11, 12, 13, 14, 15, or 20° C. lower than the thermal melting point ($T_m$). Using the equation, hybridisation and wash compositions, and desired $T_m$, those of ordinary skill will understand that variations in the stringency of hybridisation and/or wash solutions are inherently described. If the desired degree of mismatching results in a $T_m$ of less than 45° C. (aqueous solution) or 32° C.

(formamide solution), the SSC concentration may be increased so that a higher temperature can be used. An extensive guide to the hybridisation of nucleic acids is found in Tijssen (*Laboratory Techniques in Biochemistry and Molecular Biology-Hybridisation with Nucleic Acid Probes*, Pt I, Chapter 2, Elsevier, N.Y., 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, $2^{nd}$ ed., Cold Spring Harbor Laboratory Press, Plainview, N.Y., 1989).

In a further embodiment, the functionally active fragment or variant comprises one or more cis-elements which represent binding targets for DOF and/or R2R3MYB proteins. It has been demonstrated that DOF transcriptional factors interact with R2R3MYB (GAMYB) transcriptional factors in vivo and cooperatively activate endosperm-specific promoters (Diaz et al., *Plant J.* 42(5): 652-62, 2005).

As set out above, the present invention contemplates the specific or preferential expression of a nucleotide sequence of interest in a plant seed. However, in one embodiment, the present invention contemplates the specific or preferential expression of a nucleotide sequence of interest in the endosperm tissue of a plant seed.

The tissues of a plant encompassed by the term "endosperm" would be readily understood by one of skill in the art. However, this term should be understood to encompass at least the nutritive tissue, characteristic of flowering plants, which nourishes the embryo. The endosperm is typically formed after the fertilisation of the polar nuclei of the central cell by a sperm nucleus. In most plants the endosperm is a transient tissue absorbed by the embryo before maturity, whereas in cereals and grasses it contains storage reserves in the mature grain and is not absorbed until after germination.

Typically, the "endosperm" includes at least five cell types, namely, the central starchy endosperm (CSE), the sub-aleurone layer (SAL), the aleurone layer (AL), the endosperm transfer layer (ETL) and the embryo-surrounding region (ESR). The characteristics of each of these cell types are described in detail in the review of Olsen et al. (*Trends in Plant Science* 4(7): 253-257, 1999).

In one embodiment, the present invention relates to a method for specifically or preferentially expressing a nucleotide sequence of interest in the nucellar projection in the endosperm tissue in a plant.

The "nucellar projection" is part of the nucellus. The nucellus is a maternal tissue that surrounds the central cell from which the endosperm develops. In cereals, the nucellus consists of three main cell types, the nucellus parenchyma cells, the nucellus epidermal cells and the nucellar projection. The nucellus parenchyma cells are completely autolysed soon after fertilisation, while the nucellar epidermis persists throughout most of seed development, but finally autolyses and forms the hyaline layer. Concomitant with the development of the nucellar epidermis, the nucellus cells in the ventral crease of grains differentiate into the nucellar projection. The nucellar projection is the terminal maternal tissue in a route along which nutrients are transported from the vascular tissue of the pericarp to the developing endosperm and embryo.

The ETL cell layer, which includes the crease aleurone, forms over the nucellar projection in cereals such as barley and wheat and is analogous to the basal endosperm transfer layer which over the chalazal pad in maize. Accordingly, in another embodiment, the present invention relates to a method for specifically or preferentially expressing a nucleotide sequence of interest in the endosperm transfer layer of a plant seed. In yet another embodiment, the present invention relates to a method for specifically or preferentially expressing a nucleotide sequence of interest in the crease aleurone of a plant seed.

As used herein, the term "plant" includes any plant that produces seeds, including dicotyledonous or monocotyledonous angiosperms and gymnosperms. In one embodiment, however, the plant is a monocotyledonous plant and/or a cereal crop plant.

As used herein, the term "cereal crop plant" may be a member of the Poaceae (grass family) that produces grain. Examples of Poaceae cereal crop plants include wheat, rice, maize, millets, sorghum, rye, triticale, oats, barley, teff, wild rice, spelt and the like. The term cereal crop plant should also be understood to include a number of non-Poaceae plant species that also produce edible grain and are known as the pseudocereals, such as amaranth, buckwheat and quinoa.

In one specific embodiment, the present invention provides a method for specifically or preferentially expressing a nucleotide sequence of interest in a barley seed. In a further embodiment, the present invention provides a method for specifically or preferentially expressing a nucleotide sequence of interest in a barley seed wherein the nucleotide sequence of interest is expressed in the barley seed at least between 10 days after pollination (DAP) and 30 DAP.

In another specific embodiment, the present invention provides a method for specifically or preferentially expressing a nucleotide sequence of interest in a rice seed. In a further embodiment, the present invention provides a method for specifically or preferentially expressing a nucleotide sequence of interest in a rice seed wherein the nucleotide sequence of interest is expressed in the rice seed at least between 7 DAP and 24 DAP.

In another embodiment, the present invention provides a method for specifically or preferentially expressing a nucleotide sequence of interest in a wheat seed.

The present invention also contemplates expression of a nucleotide sequence of interest in the seed of dicotyledonous plants. Exemplary dicotyledonous plants include, for example, *Arabidopsis* spp., *Nicotiana* spp., soybean, canola, oil seed rape, sugar beet, mustard, sunflower, potato, safflower, cassava, yams, sweet potato, other Brassicaceae such as *Thellungiella halophila*, among others.

As set out above, the present invention is predicated, in part, on effecting transcription of the nucleotide sequence of interest under the transcriptional control of a transcriptional control sequence comprising the nucleotide sequence set forth in SEQ ID NO: 1 or a functionally active fragment or variant thereof. In one embodiment, this is effected by introducing a nucleic acid molecule comprising a transcriptional control sequence comprising the nucleotide sequence set forth in SEQ ID NO: 1 or a functionally active fragment or variant thereof, into a cell of the plant seed, such that the nucleotide sequence of interest is operably connected to the transcriptional control sequence.

The nucleic acid molecule may be introduced into the seed via any method known in the art. For example, an explant or cultured plant tissue may be transformed with a nucleic acid molecule, wherein the explant or cultured plant tissue is subsequently regenerated into a mature plant which produces seed including the nucleic acid molecule; a nucleic acid may be directly transformed into a plant seed, either stably or transiently; a nucleic acid may be introduced into a seed via plant breeding using a parent plant that carries the nucleic acid molecule; and the like.

In one embodiment, the nucleic acid molecule is introduced into a plant cell via transformation. Plants may be transformed using any method known in the art that is appropriate for the particular plant species. Common methods include *Agrobacterium*-mediated transformation, microprojectile bombardment based transformation methods and direct DNA uptake based methods. Roa-Rodriguez et al. (*Agrobacterium-mediated transformation of plants*, 3$^{rd}$ Ed. CAMBIA Intellectual Property Resource, Can berra, Australia, 2003) review a wide array of suitable *Agrobacterium*-mediated plant transformation methods for a wide range of plant species. Transformation using bacteria other than *Agrobacterium* may also be used as described in Broothaerts et al. (*Nature* 433: 629-633, 2005). Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art and, accordingly, the present invention should not be considered in any way limited to the particular plant transformation methods exemplified above.

As set out above, the transcriptional control sequence of the present invention is introduced into a plant cell such that the nucleotide sequence of interest is operably connected to the transcriptional control sequence. The present invention contemplates any method to effect this. For example, a nucleotide sequence of interest may be incorporated into the nucleic acid molecule that comprises the transcriptional control sequence, and be operably connected thereto. In this way, the nucleotide sequence of interest and transcriptional control sequence are both introduced into the plant. Alternatively, the nucleic acid sequence of the present invention may be inserted into the plant genome such that it is placed in operable connection with an endogenous nucleic acid sequence. As would be recognised by one of skill in the art, the insertion of the transcriptional control sequence into the plant genome may be either by non-site specific insertion or by site-specific insertion.

The present invention also contemplates expression of a nucleotide sequence which is "heterologous with respect to SEQ ID NO: 1". A nucleotide sequence which is "heterologous with respect to SEQ ID NO: 1" should be understood to include any nucleotide sequence other than that which is operably connected to SEQ ID NO: 1 in its natural state. For example, in its natural state, SEQ ID NO: 1 is operably connected to the P0691E06.24 gene in rice (Entrez GeneID 3047524). Accordingly, in this example, any nucleotide sequence other than a nucleotide sequence encoding the rice gene P0691E06.24 should be considered heterologous with respect to SEQ ID NO: 1. As would be recognised by one of skill in the art a sequence that is "heterologous with respect to SEQ ID NO: 1" may be derived from the same organism or a different organism from which SEQ ID NO: 1 is derived.

Furthermore, as would be recognised by one of skill in the art, the nucleotide sequence of interest, which is placed under the regulatory control of the transcriptional control sequence of the present invention, may be any nucleotide sequence of interest. For example, general categories of nucleotide sequences of interest may include nucleotide sequences which encode reporter proteins, such as, GUS, GFP and the like; proteins involved in cellular metabolism such as Zinc finger proteins, kinases, heat shock proteins and the like; proteins involved in agronomic traits such as disease or pest resistance or herbicide resistance; proteins involved in grain characteristics such as grain biomass, nutritional value, post-harvest characteristics and the like; heterologous proteins, such as proteins encoding heterologous enzymes or structural proteins or proteins involved in biosynthetic pathways for heterologous products. Furthermore, the nucleotide sequence of interest may alternatively encode a non-translated RNA, for example an siRNA, miRNA, antisense RNA and the like.

In a second aspect, the present invention provides a nucleic acid construct comprising a transcriptional control sequence comprising the nucleotide sequence set forth in SEQ ID NO: 1 or a functionally active fragment or variant thereof.

The nucleic acid construct of the present invention may comprise any polyribonucleotide or polydeoxyribonucleotide, which may be unmodified RNA or DNA or modified RNA or DNA. For example, the nucleic acid construct of the invention may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid construct" embraces chemically, enzymatically, or metabolically modified forms.

In one embodiment, the nucleic acid construct comprises DNA. Accordingly, the nucleic acid construct of the present invention may comprise, for example, a linear DNA molecule, a plasmid, a transposon, a cosmid, an artificial chromosome and the like. Furthermore, the nucleic acid construct of the present invention may be a separate nucleic acid molecule or may be a part of a larger nucleic acid molecule.

In one embodiment, the nucleic acid construct further comprises a nucleotide sequence of interest, which is heterologous with respect to SEQ ID NO: 1, wherein the nucleotide sequence of interest is operably connected to the transcriptional control sequence.

In a further embodiment, the nucleic acid construct may further comprise a nucleotide sequence defining a transcription terminator.

The term "transcription terminator" or "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

In one specific embodiment, the nucleic acid construct of the present invention comprises an expression cassette having the structure:

$$([N]_w\text{-TCS-}[N]_x\text{-Sol-}[N]_y\text{-TT-}[N]_z)$$

wherein:

$[N]_w$ comprises one or more nucleotide residues, or is absent;
TCS defines a transcriptional control sequence comprising the nucleotide sequence set forth in SEQ ID NO: 1, or a functionally active fragment or variant thereof;
$[N]_x$ comprises one or more nucleotide residues, or is absent;
Sol comprises a nucleotide sequence of interest that is heterologous with respect to SEQ ID NO: 1, which encodes an mRNA or non-translated RNA, wherein the nucleotide sequence, Sol, is operably connected to the transcriptional control sequence, TCS;
$[N]_y$ comprises one or more nucleotide residues, or is absent;
TT comprises a nucleotide sequence defining a transcription terminator;
$[N]_z$ comprises one or more nucleotide residues, or is absent.

The nucleic acid constructs of the present invention may further comprise nucleotide sequences such as, an origin of replication for one or more hosts; a selectable marker gene which is active in one or more hosts and the like.

As used herein, the term "selectable marker gene" includes any gene that confers a phenotype on a cell, in which it is expressed, to facilitate the identification and/or selection of cells which are transfected or transformed with a genetic construct of the invention.

"Selectable marker genes" include any nucleotide sequences which, when expressed by a cell, confer a phenotype on the cell that facilitates the identification and/or selection of these transformed cells. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (eg. nptI and nptII) and hygromycin phosphotransferase genes (eg. hpt); herbicide resistance genes including glufosinate, phosphinothricin or bialaphos resistance genes such as phosphinothricin acetyl transferase encoding genes (eg. bar), glyphosate resistance genes including 3-enoyl pyruvyl shikimate 5-phosphate synthase encoding genes (eg. aroA), bromyxnil resistance genes including bromyxnil nitrilase encoding genes, sulfonamide resistance genes including dihydropterate synthase encoding genes (eg. suI) and sulfonylurea resistance genes including acetolactate synthase encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

The present invention extends to all genetic constructs essentially as described herein, which may include further nucleotide sequences intended for the maintenance and/or replication of the genetic construct in prokaryotes or eukaryotes and/or the integration of the genetic construct or a part thereof into the genome of a eukaryotic or prokaryotic cell.

In one embodiment, the construct of the invention is adapted to be at least partially transferred into a plant cell via Agrobacterium-mediated transformation. Accordingly, in one specific embodiment, the nucleic acid construct of the present invention comprises left and/or right T-DNA border sequences.

Suitable T-DNA border sequences would be readily ascertained by one of skill in the art. However, the term "T-DNA border sequences" should be understood to encompass any substantially homologous and substantially directly repeated nucleotide sequences that delimit a nucleic acid molecule that is transferred from an Agrobacterium sp. cell into a plant cell susceptible to Agrobacterium-mediated transformation. By way of example, reference is made to the paper of Peralta and Ream (Proc. Natl. Acad. Sci. USA, 82(15): 5112-5116, 1985) and the review of Gelvin (Microbiology and Molecular Biology Reviews, 67(1): 16-37, 2003). The present invention also contemplates any suitable modifications to the genetic construct which facilitate bacterial mediated insertion into a plant cell via bacteria other than Agrobacterium sp., for example, as described in Broothaerts et al. (supra, 2005).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an E. coli cell or a plant cell or an animal cell. Exemplary methods for cloning nucleic acid molecules are described in Sambrook et al. (Molecular Cloning: A Laboratory Manual, Cold Spring Harbor Laboratory Press, New York, 2000).

In a third aspect, the present invention provides a cell comprising a nucleic acid construct of the second aspect of the invention or a genomically integrated form thereof.

The nucleic acid construct may be maintained in the cell as a nucleic acid molecule, as an autonomously replicating genetic element (eg. a plasmid, cosmid, artificial chromosome or the like) or it may be integrated into the genomic DNA of the cell.

As used herein, the term "genomic DNA" should be understood in its broadest context to include any and all DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

The cells contemplated by the third aspect of the invention include any prokaryotic or eukaryotic cell. In various embodiments, the cell is a plant cell, a monocot plant cell, a cereal crop plant cell or a barley, rice or wheat cell. In another embodiment, the cell may also comprise a prokaryotic cell. For example the prokaryotic cell may include an Agrobacterium sp. cell which carries the nucleic acid construct and which may, for example, be used to transform a plant. In another embodiment, the prokaryotic cell may include an E. coli cell, which may, for example, be used in the construction or cloning of the nucleic acid construct.

In a fourth aspect, the present invention contemplates a multicellular structure comprising one or more cells of the third aspect of the invention.

In one embodiment, the multicellular structure comprises a plant or a part, organ or tissue thereof. As referred to herein, "a plant or a part, organ or tissue thereof" should be understood to specifically include a whole plant; a plant tissue; a plant organ; a plant part; plant reproductive material (including, for example, cuttings, seed, pollen and the like); and cultured plant tissue such as a callus or suspension culture.

In various embodiments the plant or a part, organ or tissue thereof comprises a monocot plant or a part, organ or tissue thereof, a cereal crop plant or a part, organ or tissue thereof or a barley, wheat or rice plant or a part, organ or tissue thereof.

In one embodiment, the multicellular structure comprises a plant seed. In a further embodiment a nucleotide sequence of interest is specifically or preferentially expressed in the seed. In yet further embodiments a nucleotide sequence of interest is specifically or preferentially expressed in one or more of the endosperm tissue, the nucellar projection, the Endosperm Transfer Layer (ETL) or the crease aleurone in a seed.

In a yet further embodiment, the seed comprises a monocot plant seed and in another embodiment a cereal crop plant seed. In one specific embodiment, the seed comprises a barley seed. In a yet further embodiment, the nucleotide sequence of interest is expressed in the barley seed at least between 10 DAP and 30 DAP. In another specific embodiment, the seed comprises a rice seed. In a yet further embodiment, the nucleotide sequence of interest is expressed in the rice seed at least between 7 DAP and 24 DAP. In yet another embodiment, the seed comprises a wheat seed.

In a fifth aspect, the present invention provides an isolated nucleic acid molecule comprising the nucleotide sequence set forth in SEQ ID NO: 1, or a functionally active fragment or variant thereof, wherein the nucleotide sequence defines a transcriptional control sequence.

The isolated nucleic acid molecule of the present invention may comprise any polyribonucleotide or polydeoxyribonucleotide, which may be unmodified RNA or DNA or modified RNA or DNA. For example, the isolated nucleic acid molecules of the invention may comprise single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, the isolated nucleic acid molecules may comprise triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (eg. polymerase chain reaction and the like).

Generally, the transcriptional control sequence specifically or preferentially directs the expression of an operably connected nucleotide sequence in a plant seed. In further embodiments the transcriptional control sequence specifically or preferentially directs the expression of an operably connected nucleotide sequence in one or more of the endosperm tissue, the nucellar projection, the Endosperm Transfer Layer (ETL) or the crease aleurone in a seed.

In further embodiments, the transcriptional control sequence specifically or preferentially directs the expression of an operably connected nucleotide sequence in a monocot plant seed and/or a cereal crop plant seed.

In one specific embodiment, the transcriptional control sequence specifically or preferentially directs the expression of an operably connected nucleotide sequence in a barley seed, and in a further embodiment at least between 10 DAP and 30 DAP in the barley seed.

In another specific embodiment, the transcriptional control sequence specifically or preferentially directs the expression of an operably connected nucleotide sequence in a rice seed, and in a further embodiment at least between 7 DAP and 24 DAP in the rice seed.

In another embodiment, the transcriptional control sequence specifically or preferentially directs the expression of an operably connected nucleotide sequence in a wheat seed.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

BRIEF DESCRIPTION OF THE FIGURES

FIG. 1 shows a schematic representation of the pGBT1 vector.

FIG. 2 shows an amino acid alignment of the proteins deduced from the HvEND1 (SEQ ID NO:5) and OsEND60L2 (SEQ ID NO:6) cDNA sequences. Identical amino acid residues are in black boxes, conservative amino acids and blocks of similar amino acids are indicated by grey boxes. The amino acid sequence of HvEND1 and OsEND60L2 are 48.7% identical.

FIG. 3 shows the gene sequences of OsEND60L2 (SEQ ID NO:7) with indicated cis-elements, which may be involved in the endosperm-specific activity of the PR602 promoter. Core elements of R2R3MYB factors are in bold, core elements of the prolamin box are in bold and underlined. The fragment of the gene that matches the cDNA sequence is highlighted: the CDS is in bold with the deduced amino acid sequence (SEQ ID NOS:8 and 9) over it, and the 5'UTR and 3'UTR are underlined.

EXAMPLE 1

Plant Material

Figure 4:
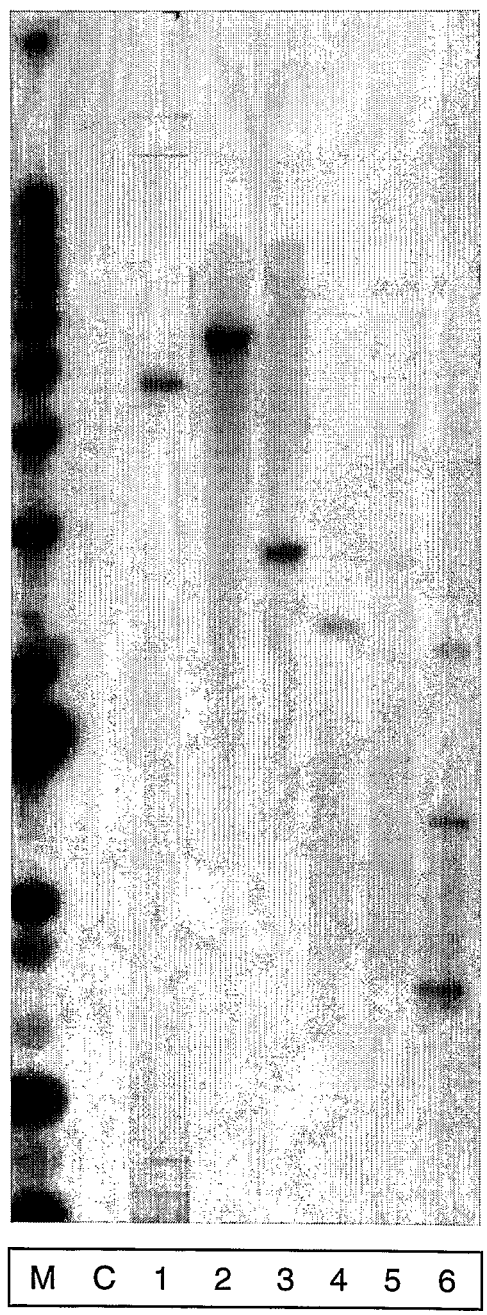
FIG. 4 shows a Southern blot confirming the successful integration of pMDC164-PR602 into transgenic plant lines. The coding region of hygromycin phosphotransferase was used as a probe. M—molecular weight markers, C—control: wild type *Hordeum vulgare* cv. Golden promise, 1—line 1, 2—line 3, 3—line 6, 4—line 2, 5—line 4, 6—line 5. The number of bands reflects number of integrated copies.

*Oryza sativa* L. ssp. *japonica* cv. Nipponbare was used for genomic DNA isolation and for the subsequent cloning of the PR602 promoter (SEQ ID NO: 1) promoter. *Hordeum vulgare* cv Golden Promise was used for transformation using *Agrobacterium tumefaciens*.

EXAMPLE 2

Isolation of Promoter Sequences and Preparation of Reporter Constructs

The amino acid sequence deduced from the barley END1 cDNA (Doan et al., *Plant Mol. Biol.* 31: 877-886, 1996) was used to identify rice homologues in the NCBI and TIGR EST databases using the TBLASTN algorithm. One rice EST (Accession No. TC226209), originating from a rice panicle cDNA library and which comprised a full-length coding region of an END1-like protein, was used to query genomic database of rice. A promoter with a full-length 5'-untranslated region of the identified END1-like gene, designated as PR602 (2809 bp; SEQ ID NO: 1), was identified and isolated by PCR using AccuPrime™ Pfx DNA polymerase (Invitrogen) and rice genomic DNA as a template.

The tetranucleotide sequence CACC was introduced into the 5' ends of the forward primers (Table 2) and the PCR product was directionally cloned into the pENTR-D-TOPO vector using pENTR Directional TOPO Cloning Kits (Invitrogen).

TABLE 2

Primer sequences used for sequencing and PCR amplification

| Primer Name | Sequence |
|---|---|
| C_PR602 | CACCACTCAAAACGAGAAAACTCATTGACAC (SEQ ID NO: 2) |
| PR602r | GGCTATTGCTTTAGTATAAAGCAGC (SEQ ID NO: 3) |
| GUS5'rev | ACTGAATGCCCACAGGCCGT (SEQ ID NO: 4) |

The construct was linearised with either EcoRV or MluI restriction enzymes and used for cloning of the promoter by recombination into the destination binary vector for plant transformation, pMDC164 (Curtis and Grossniklaus, *Plant Physiol.* 133: 462-469, 2003), upstream of a β-glucoronidase (GUS) cDNA. These constructs were used for rice and barley transformation.

For wheat transformation the same promoter is cloned into the psGFP-BAR-TOPO1 (pGBT1) vector, which is a modification of the psGFP-BAR plasmid (Richards et al., *Plant Cell Rep.* 20: 48-54, 2001) obtained by cloning of the PacI-XhoI fragment of the pMDC164 vector, containing the Gateway recombination cassette, GUS gene and nos terminator, into the unique SmaI site of the psGFP-BAR vector (FIG. 1). Overhangs of the PacI-XhoI fragment are removed before cloning into the SmaI site using Mung Bean nuclease (Amersham Biosciences).

EXAMPLE 3

Plant Transformation (i) Rice Transformation

Five-week-old secondary, seed embryo-derived callus of cv. Nipponbare (*Oryza sativa* ssp. *japonica*) was co-cultured with the *Agrobacterium* strain EHA105 or LBA4404 carrying the pMDC164-PR602 binary plasmid following the procedure detailed in Sallaud et al. (*Theor. Appl. Genet.* 106: 1396-1408, 2003).

Dehulled seeds were sterilised, inoculated on NB medium and incubated for 18-21 days in the dark as described in Chen et al. (*Plant Cell Rep.* 18: 25-31, 1998). Embryogenic nodular units (0.5-1 mm long), released from the primary embryo scutellum-derived callus at the explant/medium interface, were transferred onto fresh NB medium and incubated for an additional 10-15 days depending on the variety.

Between 50 and 100 3- to 5-mm-long embryogenic nodular units were immersed into 25 ml of liquid co-culture medium (CCL) containing *Agrobacterium* cells at a density of $3\text{-}5\times10^9$ cells $ml^{-1}$ ($OD_{600}=1$) in a 100-mm-diameter petri dish for 10-15 min. Ten callus pieces were then blotted dry on sterilised filter paper, transferred to a petri dish containing solid co-culture medium (CCS) and incubated for 3 days at 25° C. in the dark. Five to seven uncontaminated co-cultured calli were then individually transferred to one dish of R2S (Ohira et al., *Plant & Cell Physiol.* 14: 1113-1121, 1973) selection medium, which contained hygromycin for selection of transformed tissues and cefotaxime and vancomycin for eliminating *Agrobacterium*, and incubated at 27° C. in the dark.

Following 2 weeks of selection on R2S medium, the calli were transferred to NBS medium. After 1 week of incubation, the protuberances developed into brownish globular structures, which were gently teased apart with forceps on the medium around the original callus and incubated for 10-15 days in the resealed petri dish. Five weeks after co-culture, the globular structures had evolved into round shaped, compact, opaque and yellowish calli.

The putatively transgenic, hygromycin-resistant calli were gently picked out, placed on the PRAG pre-regeneration medium and incubated for a further week. All of the resistant calli originating from a single co-cultured embryogenic nodular unit were grouped in a sector of the PRAG dish, which can accommodate 40-50 resistant calli.

Four to five, creamy-white, lobed calli with a smooth and dry appearance were individually transferred to one dish of RN regeneration medium, kept for 2 days in the dark, then maintained for 3 weeks under a 12/12-h (day/night) photoperiod. Shoots regenerating from a resistant callus were dissected and sub-cultured in test tubes containing P medium for a further 3-week growth period to promote vigorous tiller and root development before being transferred to Jiffy peat pellets in the containment greenhouse for acclimatisation.

(ii) Barley Transformation

*Agrobacterium tumefaciens*-mediated transformation of barley (*Hordeum vulgare* cv Golden Promise) was performed with plasmid pMDC164-PR602 using the procedure developed by Tingay et al. (*Plant J.* 11: 1369-1376, 1997) and modified by Matthews et al. (*Mol. Breed.* 7: 195-202, 2001).

Developing spikes were harvested from donor plants grown in the glasshouse when the immature embryos are approximately 1-2 mm in diameter. The immature embryos were aseptically excised from the surface-sterilised grain, and the scutella were isolated by removing the embryonic axes.

Twenty five freshly isolated scutella were cultured cut side-up in the centre of a 90 mm×10 mm Petri dish containing callus induction medium, based on the recipe of Wan and Lemaux (*Plant Physiol.* 104: 37-48, 1994). This medium is composed of MS macro-nutrients (Murashige and Skoog, *Physiol. Plant.* 15: 473-497, 1962), FHG micro-nutrients (Hunter, Plant regeneration from microspores of barley, *Hordeum vulgare*, Ph.D thesis, Wye College, University of London, Ashford, Kent, 1988), supplemented with 30 g/L maltose, 1 mg/L thiamine-HCl, 0.25 g/L myo-inositol, 1 g/L casein hydrolysate, 0.69 g/L L-proline, 10 μM CuSO4, 2.5 mg/L Dicamba (3,6-dichloro-o-anisic acid), and is solidified with 3.5 g/L Phytagel (Sigma Chemicals, St. Louis, Mo., USA).

*Agrobacterium* suspension (50 ml) was aliquotted onto the scutella, and the Petri dish was held at a 45° angle to drain away excess bacterial suspension. The explants were then turned over and dragged across the surface of the medium to the edge of the Petri dish. The scutella were transferred to a fresh plate of callus induction medium and cultured cut side-up for three days in the dark at 22-24° C.

Following co-cultivation, the scutella were removed to fresh callus induction medium containing 95 μM hygromycin B (Becton Dickinson Biosciences, Palo Alto, Calif., USA) and cultured in the dark. The entire callus of an individual scutellum was transferred to fresh selection medium every fortnight for a further six weeks. At the end of the callus selection period, the callus derived from each treated scutellum was transferred to shoot regeneration medium. This medium is based on the FHG recipe of Wan and Lemaux (1994, supra). It contains FHG macro- and micro-nutrients (Hunter, 1988, supra), 1 mg/L thiamine-HCl, 1 mg/L benzylaminopurine (BAP), 0.25 g/L myo-inositol, 0.73 g/L L-glutamine, 62 g/L maltose, 10 μM CuSO4, 38 μM hygromycin B, and is solidified with 3.5 g/L Phytagel. The cultures were exposed to light (16 h day/8 h night photo-period) for three to four weeks at 22-24° C. The regenerated shoots were excised from the callus and transferred to culture boxes (Magenta Corporation, Chicago, Ill., USA) that contained hormone-free callus induction medium, supplemented with 95 μM hygromycin B to induce root formation. The tissue culture-derived plants were finally established in soil and grown to maturity.

All the media contain 150 mg/L Timentin (SmithKline Beecham, Pty. Ltd., Melbourne, Australia) to inhibit the growth of *Agrobacterium tumefaciens* following co-cultivation. Presence of inserts in transgenic lines was confirmed by Southern blot hybridisation using a 1.1 kb fragment of the hygromycin phosphotransferase gene (hpt) (amplified from the vector pCAMBIA1380) as a probe.

(iii) Wheat Transformation

Immature embryos of the Russian wheat variety Andros are cultured on MS medium supplemented to a final concentration of 2 mg $l^{-1}$ 2,4-D. After a 5-13 day preculture period, explants are transferred to MS medium, supplemented with 0.4 M mannitol, for 4 h prior to bombardment. A particle inflow gun built according to the design of Finer et al. (*Plant Cell Rep.* 11: 323-328, 1992) is used to deliver tungsten particles coated with plasmid construct psGBT1-PR602 into the immature embryo-derived callus.

Eleven hours post-bombardment the embryos are transferred onto selection medium containing 3 mg $l^{-1}$ phosphinotricin (PPT). GFP-expressing calli are subcultured onto fresh medium at 2-3 week intervals. Visual selection for GFP expressing sectors is performed using a fluorescence stereomicroscope Opton ICM 405. The filter set used consists of the excitation filter 450/490 (450-490 nm) combined with the barrier filter 515/530 (515-530 nm). Only calli showing GFP expression are transferred to fresh medium at each subculture. After 6-8 weeks of culture, shoots obtained on PPT-regeneration medium showing GFP expression are rooted in Magenta boxes and then transferred to a greenhouse.

EXAMPLE 4

β-Glucuronidase Assays

β-glucuronidase activity in transgenic barley and rice plants was analysed by Histochemical staining using the chromogenic substrate 5-bromo-4-chloro-3-indolyl-β-glucuronic acid (X-Gluc) (BioVectra) as described by Hull and Devic (Methods Mol. Biol. 49:125-41, 1995). Different plant organs, whole grain and grain sections of different ages were immersed in a 1 mM X-Gluc solution in 100 mM sodium phosphate, pH 7.0, 10 mM Na EDTA, 2 mM $FeK_3(CN)_6$, 2 mM $K_4Fe(CN)_6$ and 0.1% Triton X-100. After vacuum infiltration at ~26 inch Hg for 20 min, the samples were incubated at 37° C. until satisfactory staining was observed. Tissues were incubated in 20%, 35%, 50%, fixed in FAA and cleared in 70% ethanol. The whole-mount grains were then observed under the dissecting microscope and photographs were taken. The grain sections were continued dehydrating in 80%, 90% and incubated in 95% ethanol with the counter stain Eosin Y for a better contrast. Both longitudinal and transverse sections of the tissues were embedded in paraffin wax, sectioned at 10-12 µm, de-paraffinised and mounted in DPX (Fluka Biochemika) as described in Weigel and Glazebrook (*ARABIDOPSIS A Laboratory Manual*, p. 243-248, Cold Spring Harbor Laboratory Press, 2002). Then specimen were observed under the dissecting microscope (ZEISS, Stemi) and photographed with SPOT digital camera (SciTech Pty).

EXAMPLE 5

Isolation of Promoter Sequences and Generation of Constructs

A rice EST, designated OsEND60L2 (Accession No. TC226209), which contained a full length sequence of the coding region of an END1-like gene, was selected. OsEND60L2 originated from a cDNA library prepared from the rice panicle at flowering (TIGR #C47). Alignment of the deduced amino acid sequence of OsEND60L2 and the barley END1 protein is shown in FIG. 2.

The nucleotide sequence of the EST was used to identify the possible transcriptional and translational start of the gene. A 2809 bp long DNA fragment upstream of the translational start of the OsEND60L2 (FIG. 3) was isolated from rice genomic DNA using PCR. A proof-reading polymerase was used to achieve high-fidelity amplification of the promoter sequences and to obtain blunt end products for directional cloning into pENTR-D-TOPO.

The DNA fragment comprising the promoter was then sequenced and used for cloning into either the binary vector pMDC164 or the vector pGBT1 for transformation by bombardment. pGBT1 was generated by cloning of part of the pMDC164 vector into pSGFP-BAR. The pGBT1-derived construct was successfully used in the study of PR602 promoter activity, confirming this vector to be a useful tool for promoter-GUS expressional studies in wheat and other plants that are transformed by bombardment. It permits easy, efficient and restriction-independent cloning of promoters of several kilobase pairs in length into the relatively large plasmid.

The structure of the final promoter-containing constructs derived from the pMDC164 and pGBT1 vectors were confirmed by restriction analysis and sequencing using the primer GUS5'rev (SEQ ID NO: 4).

EXAMPLE 6

Computational Analysis for Putative Cis-Elements in PR602

Functional analysis of endosperm-specific promoters revealed several conserved cis-elements. Among them are the GCN4-like motif (GLM; 5'-ATGAG/CTCAT-3') recognised by bZIP proteins of the Opaque2 subfamily (as described in Albani et al., *Plant Cell* 9(2): 171-184, 1997; Onate et al., *J. Biol. Chem.* 274(14): 9175-9182, 1999; Vicente-Carbajosa et al., *Plant J.* 13(5): 629-640, 1998; Wu et al., *Plant J.* 1998 14(6): 673-83, 1998), the prolamin box (PB; 5'-TGTAAAG-3') bound by one zinc finger (DOF) class of transcription factors (as described in Lijavetzky et al., *BMC Evol Biol.* 3: 17, 2003; Vicente-Carbajosa et al., *Proc. Natl. Acad. Sci. USA*. 94(14): 7685-7690, 1997; Yanagisawa, *Trends Plant Sci*. 7(12): 555-560, 2002; Yanagisawa, *Plant Cell Physiol*. 45(4): 386-391, 2004) and a motif for the R2R3MYB class of transcription factors (5'-AAC/TA-3') (as described by Diaz et al., *Plant J*. 29(4): 453-464, 2002; Suzuki et al., *Plant Cell Physiol*. 39(5): 555-559, 1998).

It has been demonstrated DOF transcriptional factor(s) interact with R2R3MYB (GAMYB) transcriptional factors in vivo and cooperatively activate endosperm-specific promoters (Diaz et al., 2005, supra). Core sequences of multiple potential cis-elements for DOF and R2R3MYB proteins were identified in PR602 (SEQ ID NO: 1), as shown in FIG. 3.

EXAMPLE 7

Activity of Rice Promoters PR602 in Rice, Wheat and Barley

Three agriculturally important crop plants, rice, wheat and barley, were used to determine the expression pattern of the PR602 (SEQ ID NO: 1) promoter.

(i) PR602 Expression Pattern in Barley

Six putative transgenic barley lines were obtained which expressed PR602::GUS. All transformants were confirmed by Southern blot analysis (FIG. 4). Roots, stems, leaves, flowers and grain at different stages of development were stained for GUS activity.

Figure 5:
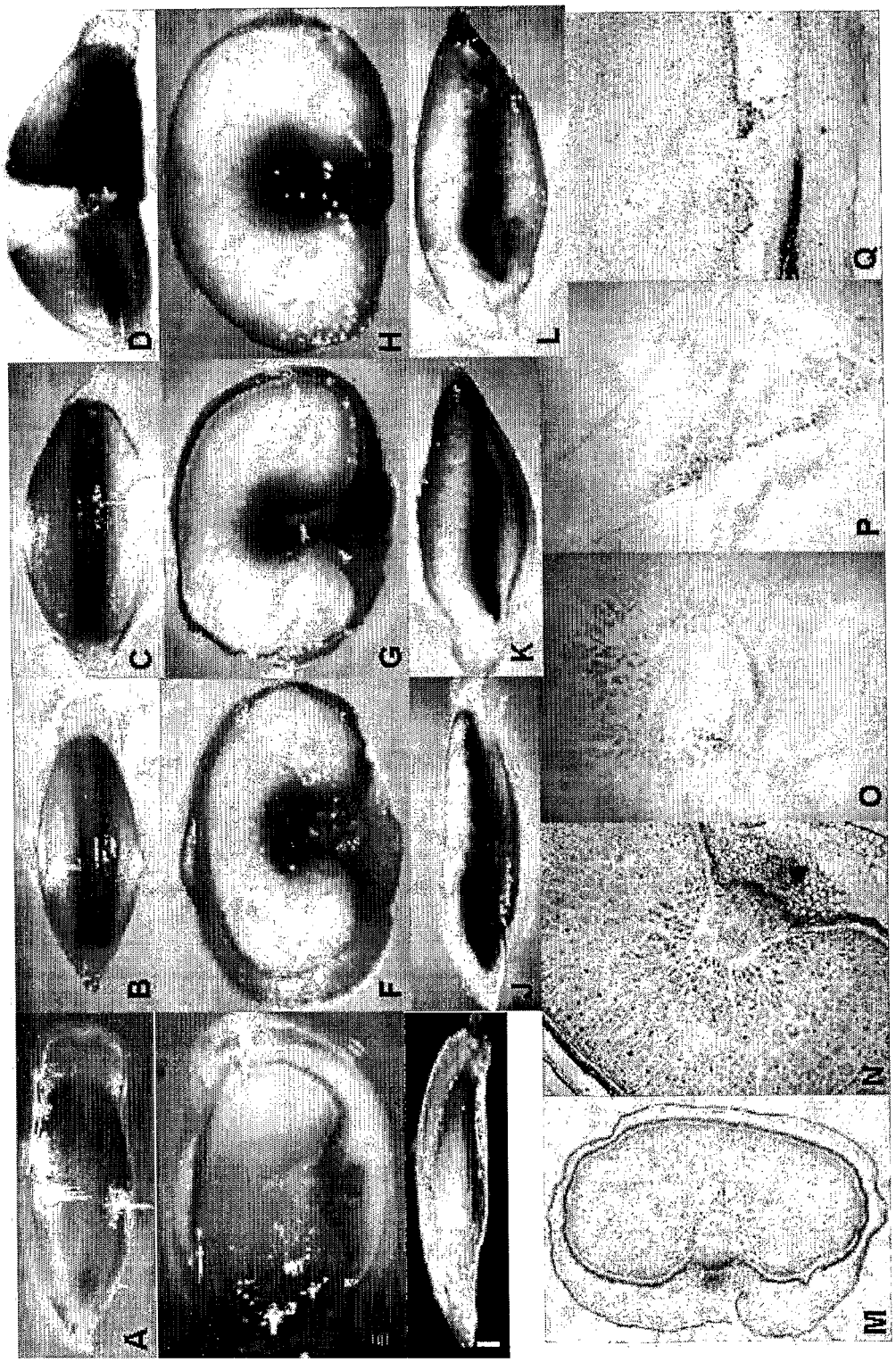
FIG. 5 shows the expression pattern of GUS in $T_1$ PR602::GUS transformed plants and wild type barley (*Hordeum vulgare* cv. Golden Promise). Panels A, E and I show GUS-assayed wild type *Hordeum vulgare* cv. Golden Promise developing grains at 10 DAP (25× magnification); panels B, F and J show GUS assayed grain derived from a PR602::GUS $T_1$ transformed plant at 10 DAP (40× mag.); panels C, G and K show GUS assayed grain derived from a PR602::GUS $T_1$ transformed plant at 16 DAP (25× mag.); and panels D, H and L show GUS assayed grain derived from a PR602::GUS $T_1$ transformed plant at 21 DAP. Panels A to D show whole grains, including the ventral groove, while panels E to H are transverse sections and panels I to L are longitudinal sections. Panels M and N show transverse sections of GUS-assayed grain derived from a PR602::GUS T$_1$ transformed plant at 10 DAP counterstained with Safranin Orange (M: 40× mag.; N: 63× mag.); panels O and P show dissected, GUS-assayed grain derived from a PR602::GUS T$_1$ transformed plant at 10 DAP at 100× mag.; while panel Q shows a dissected, GUS-assayed grain derived from a PR602::GUS T$_1$ transformed plant at 10 DAP counterstained with Eosin Y before embedding.
Figure 6:
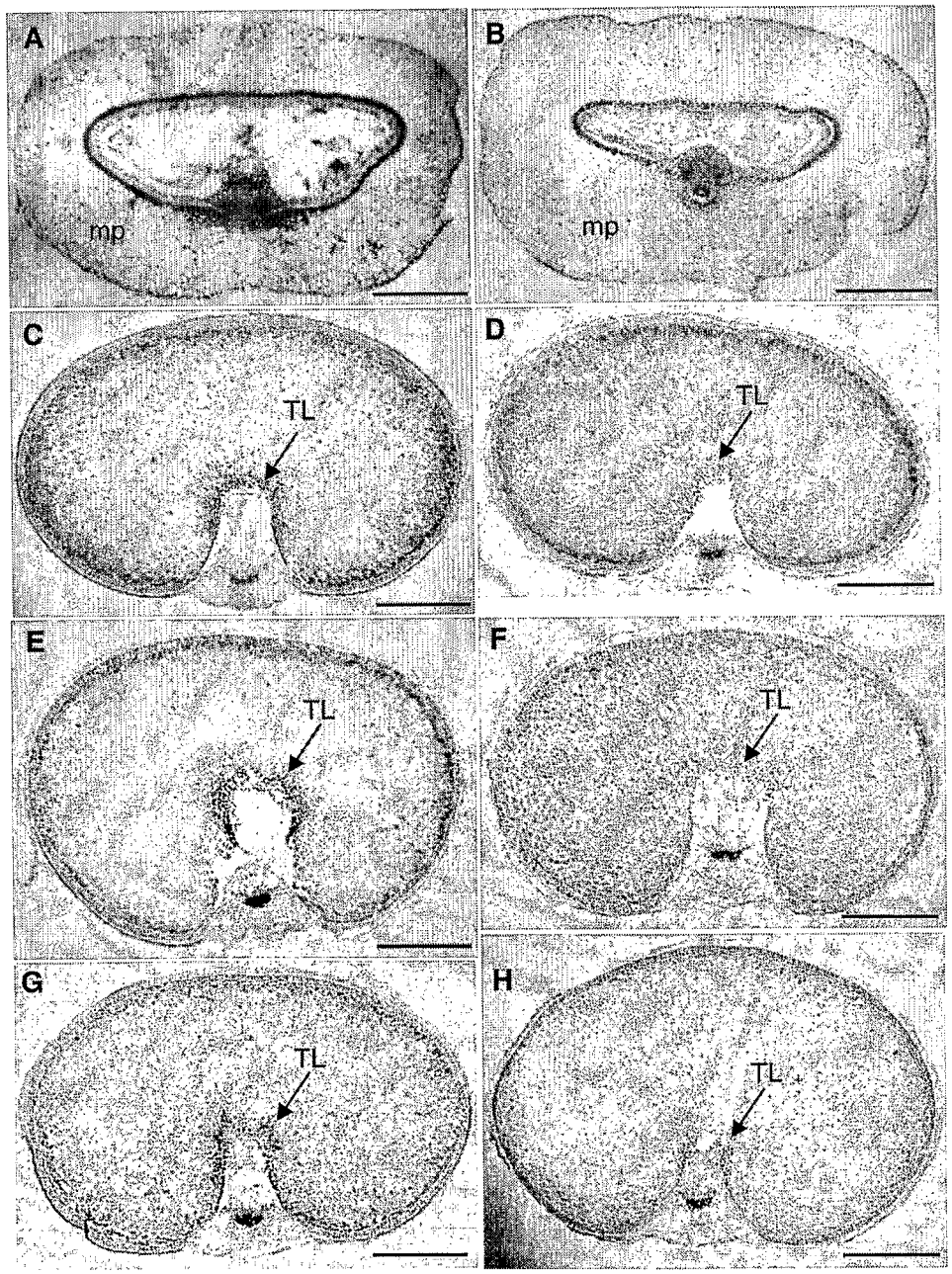
FIG. 6 shows the expression of GUS in transverse sections of grain derived from T$_1$ PR602::GUS transformed plants and wild type barley (*Hordeum vulgare* cv. Golden Promise). Panels A, C, E and G show GUS stained transverse sections of PR602::GUS transformed developing grains at 7, 10, 23 and 30 DAP, respectively. Panels B, D, F and H show GUS stained transverse sections of wild type developing grains at 7, 16, 23 and 30 DAP, respectively. mp-maternal pericarp; TL-transfer layer. Bars=1 mm'
Figure 7:
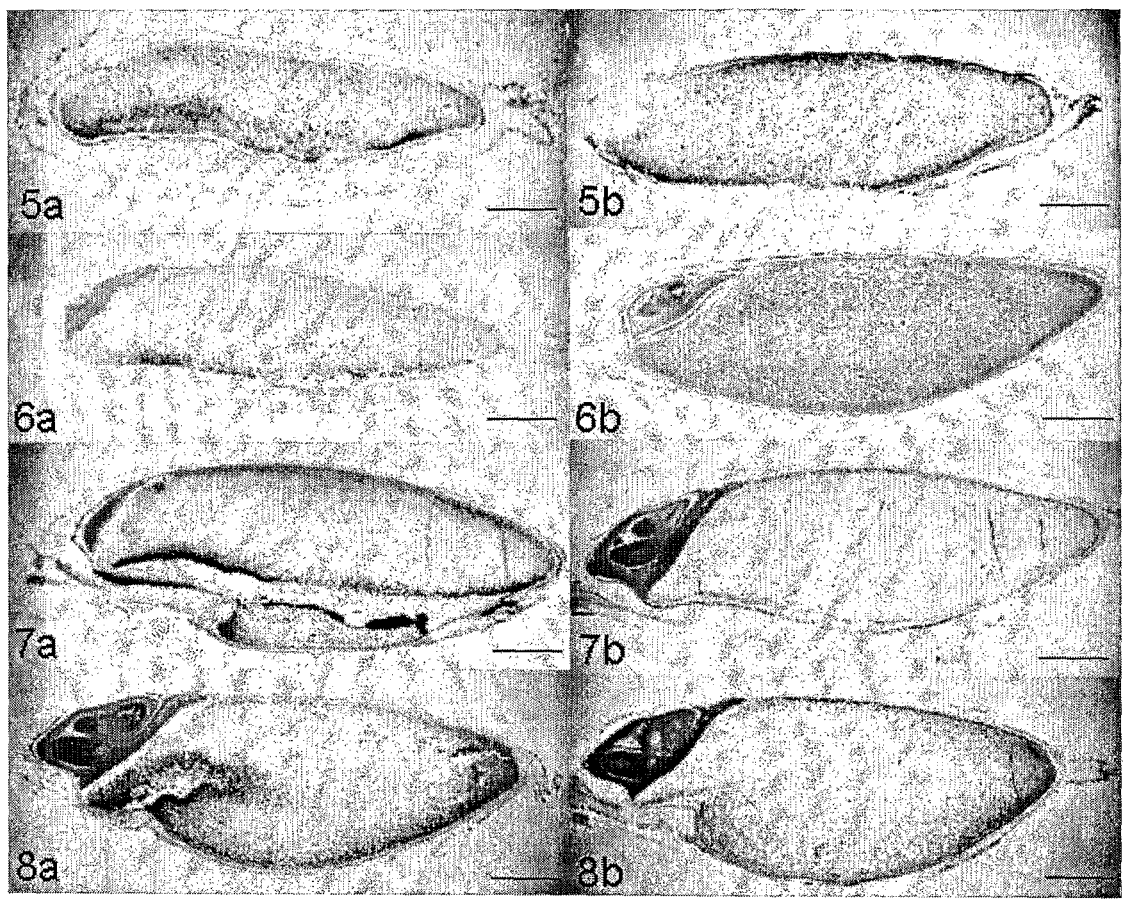
FIG. 7 shows the expression of GUS in longitudinal sections of grain derived from T$_1$ PR602::GUS transformed plants and wild type barley (*Hordeum vulgare* cv. Golden Promise). Panels 5a to 8a show GUS stained longitudinal sections of PR602::GUS transformed developing grain at 10, 16, 23 and 30 DAP, respectively. Panels 5b to 8b show GUS stained longitudinal sections of wild type developing grain at 10, 16, 23 and 30 DAP, respectively. Bar=1 mm.

As shown in FIGS. 5, 6 and 7, promoter activity (observed as GUS staining) was observed in PR602::GUS transformed lines. Prominent expression was observed in the nucellar projection of the seed and in the endosperm transfer layer around the nucellar projection in transformed plants. Expression of GUS under the control of the PR602 promoter was observed at least between 10 DAP and 30 DAP.

(ii) PR602 Expression Pattern in Rice

Figure 8:
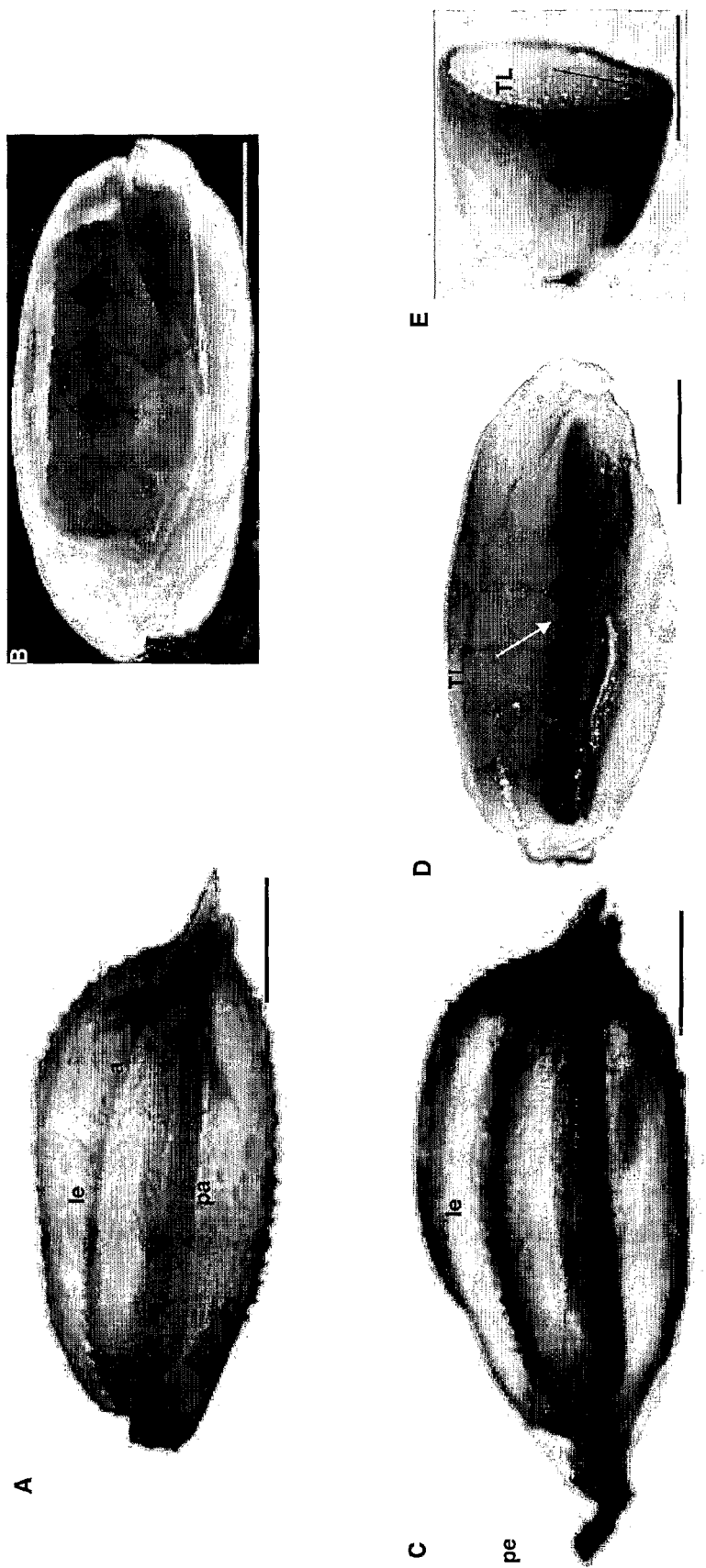
FIG. 8 shows GUS expression in the whole-mount stained PR602::GUS transgenic rice T$_0$ plants. Wild type (WT) Nipponbare floret at anthesis (A) and caryopsis longitudinally cut through the mid-grain at 18 DAP (B). PR602::GUS was expressed in the pedicel and vascular tissues of lemma and palea at anthesis (C), the transfer cell layers of caryopses at 15 DAP (D) and transverse cut at 7 DAP (E). a—anther; le—lemma; pa—palea; pe—pedicel; TL—transfer cell layers. Bars=1 mm.
Figure 9:
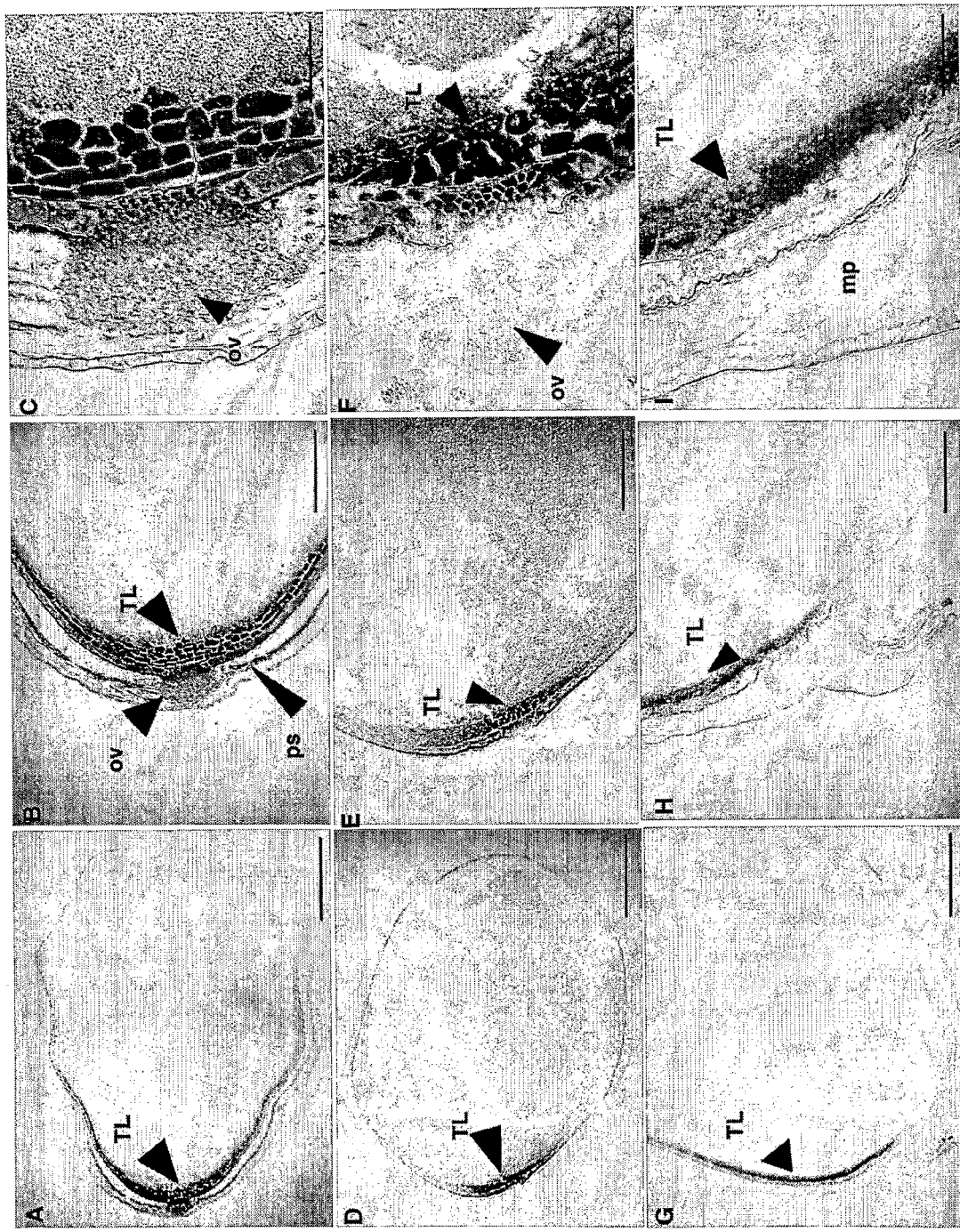
FIG. 9 shows Histological GUS expression patterns of PR602::GUS in transgenic T$_1$ rice caryopses. (A), (B) and (C)—transverse section of a developing caryopsis at 9 DAP, showing GUS activity in the transfer cell layers, nucellus, chalaza pad and pigment strand and the ovular vascular trace. (D), (E) and (F)—GUS was observed in the transfer cell layers and nucellar epidermis in a transverse section of the caryopsis at 13 DAP. (G), (H) and (I)—GUS was expressed in a longitudinal section of a caryopsis at 15 DAP. mp-maternal pericarp; ov—ovular vascular trace; ps—pigment strand; tl—transfer cell layers. Bars in (A), (D) and (G)=800 μm, bars in (B), (E) and (H)=400 μm, bars in (C), (F) and (I)=100 μm.

GUS activity was detected in PR602::GUS transgenic $T_0$ rice plants. GUS expression was found in the vascular tissues of lemma and palea at anthesis (see FIG. 8D) and GUS was predominantly expressed in the endosperm transfer cell layers starting from 7 DAP until 24 DAP in $T_1$ rice caryopsis (see FIGS. 8 and 9). Shortly after switched on, PR602 activity was also found in the ovular vascular trace, pigment strand and chalaza pad adjacent to the endosperm transfer cell layers in $T_1$ rice grain from 7-12 DAP (FIG. 9A-9C). From 13-24 DAP, GUS activity was retained only in the 3-4 layer of endosperm transfer cells shown in FIG. 9D-9I.

(iii) PR602 Expression Pattern in Wheat

Transgenic wheat lines for PR602 which exhibit expression of GFP are selected for further analysis. These plants are then analysed for GUS activity. GUS activity is expected in the region of cellularised endosperm surrounding the nucellar projection. Pre-incubation of grain at 55° C. and following staining at the same temperature may be used to decrease endogeneous GUS-like activity without a visible effect on the activity of the heterologous GUS. Plants overexpressing GUS under the constitutive rice actin (pAct) promoter are used as a positive control for quantification of GUS activity before and after incubation at 55° C.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a nucleotide sequence of interest" includes a single nucleotide sequence as well as two or more nucleotide sequences; "a plant cell" includes a single cell as well as two or more cells; and so forth.

The claims defining the invention are as follows:

1. A method for specifically or preferentially expressing a nucleotide sequence of interest in a plant seed, the method comprising effecting transcription of the nucleotide sequence of interest in a plant under the transcriptional control of a transcriptional control sequence comprising:
   (i) the nucleotide sequence set forth in SEQ ID NO: 1, or
   (ii) a nucleotide sequence that is at least 95% identical to SEQ ID NO: 1 over the full length of SEQ ID NO: 1;
   wherein the nucleotide sequence of interest is heterologous with respect to the transcriptional control sequence, and wherein the nucleotide sequence of interest is specifically or preferentially expressed in starchy endosperm cells of the plant seed.

2. A method according to claim 1 wherein the plant seed is a monocot plant seed.

3. A method according to claim 1 wherein the plant seed is a cereal crop plant seed.

4. A method according to claim 1, wherein the plant seed is a seed from a rice or barley plant.

5. A method according to claim 1, wherein the plant seed is a seed from a rice plant, and wherein the nucleotide sequence of interest is also specifically or preferentially expressed in vascular bundles of the lemma and palea, pistils and rachilla prior to fertilisation of the rice plant seed, nuclear projection cells and/or dorsal vascular bundle cells of the rice plant seed.

6. A method for specifically or preferentially expressing a nucleotide sequence of interest in a plant seed, the method comprising effecting transcription of the nucleotide sequence of interest in a plant under the transcriptional control of a transcriptional control sequence comprising:
   (i) the nucleotide sequence set forth in SEQ ID NO: 1, or
   (ii) a nucleotide sequence that is at least 95% identical to SEQ ID NO: 1 over the full length of SEQ ID NO: 1;
   wherein the nucleotide sequence of interest is heterologous with respect to the transcriptional control sequence, and wherein the nucleotide sequence of interest is specifically or preferentially expressed in starchy endosperm cells and/or endosperm transfer layer cells of the plant seed, and wherein the plant seed is a seed from a barley, wheat, maize, millets, sorghum, rye, triticale, oats, teff, or spelt plant.

* * * * *

SEQUENCE LISTING

```
<160> NUMBER OF SEQ ID NOS: 9

<210> SEQ ID NO 1
<211> LENGTH: 2809
<212> TYPE: DNA
<213> ORGANISM: Oryza sativa
<220> FEATURE:
<221> NAME/KEY: promoter
<222> LOCATION: (1)...(2809)
<223> OTHER INFORMATION: rice Japonica Group cultivar Nipponbare PR602
      promoter, operably linked to P0691E06.24 gene, DNA fragment
      upstream of translational start of OsEND60L2 EST, transcriptional
      control sequence (TCS)

<400> SEQUENCE: 1
gcactcaaaa cgagaaaact cattgacacg tgattaatta agtattaatc tctatatctt      60
ctctactatt ataaaaactg aagaagtatt tgtcagtaat ttggtacatc atccgtgtat     120
gagttggttt ttaaattcgt tcgcttttg aaatacagaa ggtgtcgtat aagaaatata     180
tttaaaaaac tcgcatgcta acttgagacg atcggacttc taactgcagc ttatgatttt     240
ctaaaaaaaa atatgttctt tttttgcgag gaaaaagata tatgttcaag tgaattctca     300
gggagaattt cactttagct aaaccatata acaataataa tattaaaata gtctttaccc     360
gttacaacgc acgggcattt ttctagtcat ttgaaaattt taaaaatatg tttattcaaa     420
tagatctaag aacttctaaa acatatttgg acatgcaaac aatctcaagt gaaaggtcat     480
taacttcaaa gttgtagatt tcgtcgagct ctacaatttt gatataaagt tggttttcat     540
ccaacaacct catatgagaa agtggtttct aaaaaaatat gcacatatga tatgagtagg     600
tccatttcta aaggcacacc tctcaaaata aaattttaga ggtgatcgct taaggcaacc     660
gcctctagaa ttgaggaggc aattaagacg atcgcctcta aaaatctatt ttataggtga     720 tttttctaatg cagttacata gaccattcat cactagaaat caggctattt ttaaagttga     780 tctgttata tggctgcctc taaaaatcaa tgtctagtgg ttgtccatga ctgcgggtcc     840
attatatacg ttggttttct tataaactat atgtacagta acaatcacga taatttaata     900
tatgtggtct cttagtttat gtgtgtgtac ggtgtgtgta tttatttgtt tctttgcatc     960
tccataatca tggttatttt gaatggtttg tttttcaggc taccgtgttc ctgcttccct    1020
cgcttaatgc ttatgtgtcc tgccagttgc attatcacgg ataactgatc atatgccatt    1080
ttatggcttc agtcataata tattgtttta ctaagtttgt ctacatgata aagagataca    1140
catggatctc tcctaaataa agtcatcatt gatgtccaca tgcattatta tgtatgttaa    1200
tttacaagtg ataaaacaca tactactact acacccaaga tgtggtatag ctcaaacaca    1260
ccccaacgta gtaattttc tagtgagaga acaatcatat atagcaaaat atcctattga    1320
gcctggcgat aataactcat agtaataatt ttattatgta agaagtttgt ttttagttat    1380
cacacacact gggtgcatct taatgctata tatttatttg gccacacaaa agtagttctt    1440
cctctaatgc ctttcattct caactttcat catttatttg tccttttttgt taggttccgt    1500
```
caacctaata tgggtgaaaa gacagttttc tattaatatg ttttaatgca agatctgtga    1560
tttttatatt ttcttttgag ttacaatttt tatactagct tattatgcat gatggtcgaa    1620
tatctctcat gaaccataat attattttag taatcaagtg tgatgcaaaa tcctttaaat    1680
ttagtatatt acataaaaaa ataattctca atttctactt cttagcttat aggctgtgcg    1740
catatagaat ttgaatttta gaagtttaa agttgatttt ggttttttat catatttatt    1800
tttagcactg acttttgaat agctaaaatt gaaaaactta tcgtaaaaaa tattattatt    1860
ggttgcttcg tttattctgg atgcatctta acatttactg taaaaatata acctatggtt    1920
tacttatatt taatcaacaa tatttattgt taaaagtaa tagacaagag aaaaacaatc    1980
ttttcttcca tctattaaca ttatgttaat ggacaactaa cggaagggc aaataagata    2040 tcaaatttaa gaataagtgt ataagagggg aagccaattt tgtgagaata aataaggaac    2100
cgatcaagtc tagaggacac ataaagaatt ttctcatcat ggtgttcata taactagccc    2160
gttgaactgt gagattgaat acttttggga tagtgaaaga atatttgact taatattttt    2220
cttgaacact acaatctgct atttgtttca catataaaaa agtgaatatt gcatcctcaa    2280
taaatgatct aacataaggt acataaatat ctaaatcttt ctctattaat gtgtcataca    2340
tggatgcata tatcttagta aatatctaaa tctttctcta ttaatgtgtg gattcataca    2400
tggatgcata tatcttcaat aagtgagtag taaatatcta aatctttctc tattaatgtg    2460
tggattcata catggatgca tatatcttca ataaatgagt agcaaatgtt taaatctttt    2520
ctttattaat gtgtgggttc aacatgcatg gatgcatata tctttaataa atgagccaat    2580
taaatatgag gtgcacaaat atccaaatct ttgcatgcat aggctctctc ttcaccattg    2640
attttacatc caatggatac aattcgagca acatgtcaac ttttcccctc gatggcctta    2700
tataaaccca actatcccca actagaagat acacaccaca acaatatagc cactgtattg    2760
atatcaagaa aaaggtctat cctagctgct ttatactaaa gcaatagcc              2809

<210> SEQ ID NO 2
<211> LENGTH: 31
<212> TYPE: DNA
<213> ORGANISM: Artificial Sequence
<220> FEATURE:
<223> OTHER INFORMATION: synthetic PCR amplification and sequencing
      forward primer C_PR602

<400> SEQUENCE: 2
caccactcaa aacgagaaaa ctcattgaca c                                   31

<210> SEQ ID NO 3
<211> LENGTH: 25
<212> TYPE: DNA
<213> ORGANISM: Artificial Sequence
<220> FEATURE:
<223> OTHER INFORMATION: synthetic PCR amplification and sequencing
      primer PR602r

<400> SEQUENCE: 3
ggctattgct ttagtataaa gcagc                                          25

<210> SEQ ID NO 4
<211> LENGTH: 20
<212> TYPE: DNA
<213> ORGANISM: Artificial Sequence
<220> FEATURE:
<223> OTHER INFORMATION: synthetic PCR amplification and sequencing
      primer GUS5'rev

```
<400> SEQUENCE: 4
actgaatgcc cacaggccgt                                                  20

<210> SEQ ID NO 5
<211> LENGTH: 107
<212> TYPE: PRT
<213> ORGANISM: Hordeum vulgare
<220> FEATURE:
<223> OTHER INFORMATION: barley END1 (HvEND1) cDNA deduced protein

<400> SEQUENCE: 5

Met Ala Lys Leu Met Cys Leu Cys Phe Ile Ile Leu Thr Ile Ala Val
 1               5                  10                  15

Val Val Ser Ala Gly Gly Cys Asp Gly Asp Arg Glu Asp Met Ile Arg
            20                  25                  30

Glu Cys Gly Lys Tyr Gln Lys Phe Pro Ala Glu Pro Lys Leu Ala Pro
        35                  40                  45

Ser Asp Ala Cys Cys Val Val Trp His Lys Ala Asn Ile Pro Cys Leu
    50                  55                  60

Cys Ala Gly Val Thr Lys Glu Lys Glu Lys Ile Trp Ser Met Glu Lys
65                  70                  75                  80

Val Gly Tyr Val Ala Asn Phe Cys Lys Lys Pro Phe Pro His Gly Tyr
                85                  90                  95

Asn Cys Gly Ser Tyr Thr Phe Pro Pro Leu Ala
            100                 105

<210> SEQ ID NO 6
<211> LENGTH: 112
<212> TYPE: PRT
<213> ORGANISM: Oryza sativa
<220> FEATURE:
<223> OTHER INFORMATION: rice OsEND60L2 cDNA (OsEND60L2_TC226209)
      deduced protein

<400> SEQUENCE: 6

Met Gly Lys Leu Tyr Gly Leu Phe Trp Val Met Ala Leu Val Leu Ala
 1               5                  10                  15

Thr Val Ala Gly Thr Lys Ser Asp Glu Gly Cys Ser Arg Asp Leu Gln
            20                  25                  30

Asp Leu Ile Met Glu Cys Gln Lys Tyr Val Met Asn Pro Ala Asn Pro
        35                  40                  45

Lys Ile Glu Pro Ser Asn Ala Cys Cys Ser Val Ile Gln Lys Ala Asn
    50                  55                  60

Val Pro Cys Leu Cys Ser Lys Val Thr Lys Glu Ile Glu Lys Ile Val
65                  70                  75                  80

Cys Met Glu Lys Val Val Tyr Val Ala Asp Tyr Cys Lys Lys Pro Leu
                85                  90                  95

Gln Pro Gly Ser Lys Cys Gly Ser Tyr Thr Ile Pro Ser Leu Gln Gln
            100                 105                 110

<210> SEQ ID NO 7
<211> LENGTH: 3530
<212> TYPE: DNA
<213> ORGANISM: Oryza sativa
<220> FEATURE:
<223> OTHER INFORMATION: rice OsEND60L2 gene sequence
<220> FEATURE:
<221> NAME/KEY: prim_transcript
<222> LOCATION: (2753)...(3416)
<223> OTHER INFORMATION: OsEND60L2 cDNA
<220> FEATURE:
```

```
<221> NAME/KEY: 5'UTR
<222> LOCATION: (2753)...(2809)
<220> FEATURE:
<221> NAME/KEY: exon
<222> LOCATION: (2810)..(3119)
<223> OTHER INFORMATION: exon 1
<220> FEATURE:
<221> NAME/KEY: intron
<222> LOCATION: (3120)..(3211)
<223> OTHER INFORMATION: intron 1
<220> FEATURE:
<221> NAME/KEY: exon
<222> LOCATION: (3212)..(3240)
<223> OTHER INFORMATION: exon 2
<220> FEATURE:
<221> NAME/KEY: 3'UTR
<222> LOCATION: (3241)...(3416)

<400> SEQUENCE: 7
gcactcaaaa cgagaaaact cattgacacg tgattaatta agtattaatc tctatatctt      60
ctctactatt ataaaaactg aagaagtatt tgtcagtaat ttggtacatc atccgtgtat     120
gagttggttt ttaaattcgt tcgcttttg  aaatacagaa ggtgtcgtat aagaaatata     180
tttaaaaaac tcgcatgcta acttgagacg atcggacttc taactgcagc ttatgatttt     240
ctaaaaaaaa atatgttctt tttttgcgag gaaaaagata tatgttcaag tgaattctca     300
gggagaattt cactttagct aaaccatata acaataataa tattaaaata gtctttaccc     360
gttacaacgc acgggcattt ttctagtcat ttgaaaattt taaaaatatg tttattcaaa     420
tagatctaag aacttctaaa acatatttgg acatgcaaac aatctcaagt gaaaggtcat     480
taacttcaaa gttgtagatt tcgtcgagct ctacaatttt gatataaagt tggttttcat     540
ccaacaacct catatgagaa agtggtttct aaaaaaatat gcacatatga tatgagtagg     600
tccatttcta aaggcacacc tctcaaaata aaatttttaga ggtgatcgct taaggcaacc    660
gcctctagaa ttgaggaggc aattaagacg atcgcctcta aaaatctatt ttataggtga     720
ttttctaatg cagttacata gaccattcat cactagaaat caggctattt ttaaagttga     780
tctgtttata tggctgcctc taaaaatcaa tgtctagtgg ttgtccatga ctgcgggtcc     840
attatatacg ttggttttct tataaactat atgtacagta acaatcacga taatttaata     900
tatgtggtct cttagtttat gtgtgtgtac ggtgtgtgta tttatttgtt tctttgcatc     960
tccataatca tggttatttt gaatggtttg tttttcaggc taccgtgttc ctgcttccct    1020
cgcttaatgc ttatgtgtcc tgccagttgc attatcacgg ataactgatc atatgccatt    1080
ttatggcttc agtcataata tattgtttta ctaagtttgt ctacatgata aagagataca    1140
catggatctc tcctaaaataa agtcatcatt gatgtccaca tgcattatta tgtatgttaa    1200
tttacaagtg ataaaacaca tactactact acacccaaga tgtggtatag ctcaaacaca    1260
ccccaacgta gtaattttc  tagtgagaga acaatcatat atagcaaaat atcctattga    1320
gcctggcgat aataactcat agtaataatt ttattatgta agaagtttgt ttttagttat    1380
cacacacact gggtgcatct taatgctata tatttatttg gccacacaaa agtagttctt    1440
cctctaatgc ctttcattct caactttcat catttatttg tccttttttgt taggttccgt    1500 caacctaata tgggtgaaaa gacagttttc tattaatatg ttttaatgca agatctgtga    1560
tttttatatt ttcttttgag ttacaatttt tatactagct tattatgcat gatggtcgaa    1620
tatctctcat gaaccataat attatttttag taatcaagtg tgatgcaaaa tcctttaaat    1680
ttagtatatt acataaaaaa ataattctca atttctactt cttagcttat aggctgtgcg    1740
catatagaat ttgaattttaa gaagttttaaa agttgatttt ggttttttat catatttatt    1800
```

```
tttagcactg acttttgaat agctaaaatt gaaaaactta tcgtaaaaaa tattattatt   1860
ggttgcttcg tttattctgg atgcatctta acatttactg taaaaatata acctatggtt   1920
tacttatatt taatcaacaa tatttattgt taaaaagtaa tagacaagag aaaaacaatc   1980
ttttcttcca tctattaaca ttatgttaat ggacaactac cggaaagggc aaataagata   2040
tcaaatttaa gaataagtgt ataagagggg aagccaattt tgtgagaata aataaggaac   2100
cgatcaagtc tagaggacac ataagaatt ttctcatcat ggtgttcata taactagccc   2160
gttgaactgt gagattgaat acttttggga tagtgaaaga atatttgact taatattttt   2220
cttgaacact acaatctgct atttgtttca catataaaaa agtgaatatt gcatcctcaa   2280
taaatgatct aacataaggt acataaatat ctaaatcttt ctctattaat gtgtcataca   2340
tggatgcata tatcttagta aatatctaaa tctttctcta ttaatgtgtg gattcataca   2400
tggatgcata tatcttcaat aagtgagtag taaatatcta aatctttctc tattaatgtg   2460
tggattcata catggatgca tatatcttca ataaatgagt agcaaatgtt taaatctttt   2520
ctttattaat gtgtgggttc aacatgcatg gatgcatata tctttaataa atgagccaat   2580
taaatatgag gtgcacaaat atccaaatct ttgcatgcat aggctctctc ttcaccattg   2640
attttacatc caatggatac aattcgagca acatgtcaac ttttcccctc gatggcctta   2700
tataaaccca actatcccca actagaagat acacaccaca acaatatagc cactgtattg   2760
atatcaagaa aaaggtctat cctagctgct ttatactaaa gcaatagcca tgggaaagct   2820
ttatggtttg ttctgggtta tggccttggt attggctacg gtggctggta caaaatccga   2880
tgagggttgc agtcgtgatc ttcaggactt aattatggag tgtcaaaaat atgttatgaa   2940
tcctgcaaac ccaaagatag aaccctcaaa cgcatgctgt agcgtaatcc aaaaggcaaa   3000
cgtcccatgt ttatgctcca aggtcactaa agagattgag aagatagtgt gcatggagaa   3060
ggtcgtgtat gttgctgact attgcaagaa gccactacag cctggctcca agtgtggaag   3120
taagctttaa tacaaactca acaaaagcat tttgtgttgt tttatgaatt gtcaatgata   3180
tttattattt tcttctgaat tacgtttgca ggctacacga ttccgtctct acaacaataa   3240
ttggatatga tcaagcatga agatgatggc tttgtctttt aggataagtg taatttgtga   3300
ggttgtccat tggcaataat ctattttgag tcatttgtgg ggaattgtgg ccaatgtgag   3360
tgggatattt aatattgtaa aataaatatt aaaaatgaac aaataatgtc ttttagattt   3420
tctatctttt cagatgacta gatggcgcct ctaaccttca tcttccacgt ggcggttccc   3480
cataggctct caatgacggt tgcaagtgaa tcgacgttgg aaaccgccat              3530
```

<210> SEQ ID NO 8
<211> LENGTH: 103
<212> TYPE: PRT
<213> ORGANISM: Oryza sativa
<220> FEATURE:
<223> OTHER INFORMATION: OsEND60L2 exon 1

<400> SEQUENCE: 8

Met Gly Lys Leu Tyr Gly Leu Phe Trp Val Met Ala Leu Val Leu Ala
1               5                   10                  15

Thr Val Ala Gly Thr Lys Ser Asp Glu Gly Cys Ser Arg Asp Leu Gln
            20                  25                  30

Asp Leu Ile Met Glu Cys Gln Lys Tyr Val Met Asn Pro Ala Asn Pro
        35                  40                  45

Lys Ile Glu Pro Ser Asn Ala Cys Cys Ser Val Ile Gln Lys Ala Asn

```
                50                  55                  60
Val Pro Cys Leu Cys Ser Lys Val Thr Lys Glu Ile Glu Lys Ile Val
 65                  70                  75                  80

Cys Met Glu Lys Val Val Tyr Val Ala Asp Tyr Cys Lys Lys Pro Leu
                 85                  90                  95

Gln Pro Gly Ser Lys Cys Gly
            100

<210> SEQ ID NO 9
<211> LENGTH: 8
<212> TYPE: PRT
<213> ORGANISM: Oryza sativa
<220> FEATURE:
<223> OTHER INFORMATION: OsEND60L2 exon 2

<400> SEQUENCE: 9

Tyr Thr Ile Pro Ser Leu Gln Gln
 1               5
```